(12) United States Patent
Galetto et al.

(10) Patent No.: US 11,007,224 B2
(45) Date of Patent: *May 18, 2021

(54) CD19 SPECIFIC CHIMERIC ANTIGEN RECEPTOR AND USES THEREOF

(71) Applicant: Cellectis, Paris (FR)

(72) Inventors: Roman Galetto, Paris (FR); Julianne Smith, New York, NY (US); Andrew Scharenberg, Seattle, WA (US); Cécile Schiffer-Mannioui, Villiers-sur-Marne (FR)

(73) Assignee: Cellectis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/099,614

(22) Filed: Nov. 16, 2020

(65) Prior Publication Data

US 2021/0060080 A1    Mar. 4, 2021

Related U.S. Application Data

(63) Continuation of application No. 14/891,296, filed as application No. PCT/EP2014/059662 on May 12, 2014, now Pat. No. 10,874,693, which is a continuation-in-part of application No. 13/892,805, filed on May 13, 2012, and a continuation-in-part of application No. PCT/US2013/040755, filed on May 13, 2013, and a continuation-in-part of application No. PCT/US2013/040766, filed on May 13, 2013.

(60) Provisional application No. 61/888,259, filed on Oct. 8, 2013.

(51) Int. Cl.
| | |
|---|---|
| *A61K 35/17* | (2015.01) |
| *C07K 14/725* | (2006.01) |
| *C07K 14/705* | (2006.01) |
| *C07K 16/28* | (2006.01) |
| *C12N 5/0783* | (2010.01) |
| *A61K 38/00* | (2006.01) |
| *A61K 39/00* | (2006.01) |

(52) U.S. Cl.
CPC .......... *A61K 35/17* (2013.01); *C07K 14/7051* (2013.01); *C07K 14/70517* (2013.01); *C07K 14/70521* (2013.01); *C07K 14/70578* (2013.01); *C07K 16/28* (2013.01); *C07K 16/2803* (2013.01); *C12N 5/0636* (2013.01); *A61K 38/00* (2013.01); *A61K 39/00* (2013.01); *C07K 2317/14* (2013.01); *C07K 2317/24* (2013.01); *C07K 2317/569* (2013.01); *C07K 2317/622* (2013.01); *C07K 2319/00* (2013.01); *C07K 2319/03* (2013.01); *C07K 2319/74* (2013.01); *C12N 2501/39* (2013.01); *C12N 2501/51* (2013.01); *C12N 2501/515* (2013.01); *C12N 2501/599* (2013.01); *C12N 2502/99* (2013.01); *C12N 2510/00* (2013.01)

(58) Field of Classification Search
CPC ............................................... A61K 2039/505
See application file for complete search history.

(56) References Cited

U.S. PATENT DOCUMENTS

| | | |
|---|---|---|
| 5,359,046 A | 10/1994 | Capon et al. |
| 10,363,270 B2 | 7/2019 | Galetto et al. |
| 10,874,693 B2 | 12/2020 | Galetto et al. |
| 2004/0012636 A1 | 1/2004 | Hasebe et al. |
| 2007/0286857 A1 | 12/2007 | Arthaud |
| 2008/0131415 A1 | 6/2008 | Riddell et al. |
| 2010/0272723 A1 | 10/2010 | Bernett et al. |
| 2011/0301073 A1 | 12/2011 | Gregory et al. |
| 2012/0060230 A1 | 3/2012 | Collingwood et al. |
| 2012/0222143 A1 | 8/2012 | Fahrenkrug et al. |
| 2013/0071414 A1 | 3/2013 | Dotti et al. |
| 2013/0196373 A1 | 8/2013 | Gregory et al. |
| 2013/0280220 A1 | 10/2013 | Ahmed et al. |
| 2013/0315884 A1 | 11/2013 | Galetto et al. |
| 2014/0227237 A1 | 8/2014 | June et al. |
| 2014/0349402 A1 | 11/2014 | Cooper et al. |
| 2015/0203817 A1 | 7/2015 | Galetto et al. |
| 2015/0225731 A1 | 8/2015 | McClain et al. |

(Continued)

FOREIGN PATENT DOCUMENTS

| | | |
|---|---|---|
| JP | 2015-528298 A | 7/2009 |
| WO | WO-01/87338 A1 | 11/2001 |

(Continued)

OTHER PUBLICATIONS

Yu et al. (PLoS One. 2012; 7 (3): e33340; pp. 1-15).*

(Continued)

*Primary Examiner* — Stephen L Rawlings

(74) *Attorney, Agent, or Firm* — Cooley LLP

(57) ABSTRACT

The present invention relates to chimeric antigen receptors (CAR). CARs are able to redirect immune cell specificity and reactivity toward a selected target exploiting the ligand-binding domain properties. In particular, the present invention relates to a Chimeric Antigen Receptor in which extracellular ligand binding is a scFV derived from a CD19 monoclonal antibody, preferably 4G7. The present invention also relates to polynucleotides, vectors encoding said CAR and isolated cells expressing said CAR at their surface. The present invention also relates to methods for engineering immune cells expressing 4G7-CAR at their surface which confers a prolonged "activated" state on the transduced cell. The present invention is particularly useful for the treatment of B-cells lymphomas and leukemia.

10 Claims, 6 Drawing Sheets

Specification includes a Sequence Listing.

(56) References Cited

U.S. PATENT DOCUMENTS

| | | |
|---|---|---|
| 2018/0298336 A1 | 10/2018 | Sentman |
| 2019/0209616 A1 | 7/2019 | Galetto et al. |
| 2019/0216853 A1 | 7/2019 | Galetto et al. |
| 2021/0000869 A9 | 1/2021 | Galetto et al. |
| 2021/0060079 A1 | 3/2021 | Galetto et al. |

FOREIGN PATENT DOCUMENTS

| | | |
|---|---|---|
| WO | WO-2007/043200 A1 | 4/2007 |
| WO | WO-2007/129093 A2 | 11/2007 |
| WO | WO-2007/129093 A3 | 11/2007 |
| WO | WO-2009/091826 A2 | 7/2009 |
| WO | WO-2009/091826 A3 | 7/2009 |
| WO | WO-2010/025177 A1 | 3/2010 |
| WO | WO-2010/027423 A2 | 3/2010 |
| WO | WO-2010/027423 A3 | 3/2010 |
| WO | WO-2010/132697 A2 | 11/2010 |
| WO | WO-2010/132697 A3 | 11/2010 |
| WO | WO-2012/047294 A2 | 4/2012 |
| WO | WO-2012/047294 A3 | 4/2012 |
| WO | WO-2012/050374 A2 | 4/2012 |
| WO | WO-2012/050374 A3 | 4/2012 |
| WO | WO-2012/079000 A1 | 6/2012 |
| WO | WO-2012/099973 A2 | 7/2012 |
| WO | WO-2012/099973 A3 | 7/2012 |
| WO | WO 2012/129514 A1 | 9/2012 |
| WO | WO-2013/019615 A2 | 2/2013 |
| WO | WO-2013/019615 A3 | 2/2013 |
| WO | WO-2013/040557 A2 | 3/2013 |
| WO | WO-2013/040557 A3 | 3/2013 |
| WO | WO-2013/059593 A1 | 4/2013 |
| WO | WO-2014/039523 A1 | 3/2014 |

OTHER PUBLICATIONS

Chang et al. (Structure. Jan. 7, 2014; 22 (1): 9-21).*
Alabanza et al. Mol. Ther. Nov. 1, 2017; 25 (11): 2452-2465.
Altenschmidt et al. (1997). "Specific cytotoxic T lymphocytes in gene therapy," J. Mol. Med. 75:259.
Arnould et al., "Engineering of large numbers of highly specific homing endonucleases that induce recombination on novel DNA targets," J. Mol. Biol., 355(3):443-58, Jan. 2006.
Arimondo et al., "Exploring the cellular activity of camptothecin-triple-helix-fanning oligonucleotide conjugates," Mol. Cell Biol., 26(1):324-33, Jan. 2006.
Ashwell and Klusner, "Genetic and mutational analysis of the T-cell antigen receptor," Annu. Rev. Immunol., 8(1): 139-67, Apr. 1990.
Ashwell et al., Glucocorticoids in T cell development and function, Annu Rev Immunol. 2000; 18:309-45.
Betts et al., "Sensitive and viable identification of antigen-specific CD8+ T cells by a flow cytometric assay for degranulation," J. Immunol. Methods, 281(1-2):65-78, Oct. 2003.
Bierer, B.E. et al. (1993). "Cyclosporin A and FK506: Molecular mechanism of immunosuppression and probes for transplantation biology," Curr, Opin. Immunol. 5:763-773.
Boch et al., "Breaking the code of DNA binding specificity of TAL-type III effectors," Science, 326(5959):1509-12, Dec. 2009.
Boglioli et al. Rewriting The Book of Life: A New Era in Precision Gene Editing; The Boston Consulting Group, Sep. 2015.
Boni et al., "Adoptive transfer of allogeneic tumor-specific T cells mediates effective regression of large tumors across major histocompatibility barriers," Blood, 112(12):4746-54, Dec. 2008.
Bridgeman et al., J. Immunol. Jun. 15, 2010; 184 (12): 6938-49.
Brocker et al., "Adoptive tumor immunity mediated by lymphocytes bearing modified antigen-specific receptors," Adv. Immunol., 68:257-269, Jan. 1998.
Burkhardt et al., "Igα and Igβ are functionally homologous to the signaling proteins of the T-cell receptor," Mol. Cell. Biol., 14(2): 1095-1103, Feb. 1994.
Caldas et al. Mol. Immunol. May 2003; 39 (15): 941-952.

Cambier, "Antigen and Fc receptor signaling. The awesome power of the immunoreceptor tyrosine-based activation motif (IT AM)," J. Immunol., 155(7):3281-5, Oct. 1995.
Carrasco et al., "An endoplasmic reticulum retention function for the cytoplasmic tail of the human pre-T cell receptor (TCR) alpha chain: potential role in the regulation of cell surface pre-TCR expression levels," J. Exp. Med., 193(9): 1045-58, May 2001.
CAS Registry No. 216503-57-0 (2021). Immunoglobulin G1, anti-(human CD52 (antigen)) (human-rat monoclonal CAMPATH-1H γl-chain), disulfide with human-rat monoclonal CAMPATH-1H light chain, dimer, 3 total pages.
Casset et al. (Biochem. Biophys. Res. Commun. Jul. 18, 2003; 307 (1): 198-205.
Cermak et al., "Efficient design and assembly of custom TALEN and other TAL effector-based constructs for DNA targeting," Nucleic. Acids. Res., 39(12):e82, Apr. 2011.
Chames et al., "In vivo selection of engineered homing endonucleases using double-strand break induced homologous recombination," Nucleic. Acids. Res., 33(20):e178, Jan. 2005.
Chang, H-J. et al. (2014). "Loop-sequence features and stability determinants in antibody variable domains by high-throughput experiments," Structure 22:9-21.
Chao et al., "Mechanisms of L-selectin regulation by activated T cells," J. Immunol., 159(4):1686-94, Aug. 1997.
Chen et al., Sheng Wu Gong Cheng Xue Bao. Sep. 2005; 21 (5): 686-91.
Chien et al., Proc. Natl. Acad. Sci. USA. Jul. 1989; 86 (14): 5532-5536.
Choulika et al., "Induction of homologous recombination in mammalian chromosomes by using the I-SceI system of *Saccharomyces cerevisiae*," Mol. Cell. Biol., 15(4):1968-73, Apr. 1995.
Christian et al., "Targeting DNA double-strand breaks with TAL effector nucleases," Genetics, 186(2):757-61, Oct. 2010.
Compound Report Card (2021). CHEMBL1201587, Alemtuzumab, 11 total pages.
Cooper, L.J. et al. (2012). "Good T-cells for bad B cells," *Blood* 119:2700-2702.
Cooper, Z.A. et al. (2013). "Combining checkpoint inhibitors and Braf-targeted agents against metastatic melanoma," Oncoimmunology 2:e24320-1-e24320-3.
Coutinho and Chapman, "The anti-inflammatory and immunosuppressive effects of glucocorticoids, recent developments and mechanistic insights," Mol. Cell. Endocrinol., 335(1):2-13, Mar. 2011.
Critchlow and Jackson, "DNA end-joining: from yeast to man." Trends. Biochem. Sci., 23(10):394-8, Oct. 1998.
De Angelis et al. (2009). Generation of Epstein-Barr virus-specific cytotoxic T lymphocytes resistant to the immunosuppressive drug tacrolimus (FK506), BLOOD 114:4784-4791.
De Pascalis et al. J. Immunol. 2002; 169 (6): 3076-3084.
De Plaen et al., "Identification of genes coding for tumor antigens recognized by cytolytic T lymphocytes," Methods, 12(2):125-42, Jun. 1997.
Deng et al., "Structural basis for sequence-specific recognition of DNA by TAL effectors," Science, 335(6069):720-3, Feb. 2012.
Devesa et al., "Cancer incidence and mortality trends among whites in the United States, 1947-84," J. Nat'l Cancer Inst., 79(4):701-70, Oct. 1987.
Eisenschmidt et al., "Developing a programmed restriction endonuclease for highly specific DNA cleavage." Nucleic. Acids. Res., 33(22):7039-47, Jan. 2005.
Epinat et al., "A novel engineered meganuclease induces homologous recombination in yeast and mammalian cells," Nucleic. Acids. Res., 31(11):2952-62, Jun. 2003.
Eshhar, "Tumor-specific T-bodies: towards clinical application," Cancer Immunil. Immunother., 45(3-4): 131-6, Nov.-Dec. 1997.
Final Office Action dated Nov. 4, 2019, for U.S. Appl. No. 14/891,296, filed Nov. 13, 2015, 15 pages.
Finney et al., "Activation of resting human primary T cells with chimeric receptors: costimulation from CD28, inducible costimulator, CD134, and CD137 in series with signals from the TCR zeta chain," J. Immunol., 172(1):104-113, Jan. 2004.

(56) References Cited

OTHER PUBLICATIONS

Fitzer-Attas et al., "Harnessing Syk family tyrosine kinases as signaling domains for chimeric single chain of the variable domain receptors: optimal design for T cell activation," J. Immunol., 160(1): 145-54, Jan. 1998.
Freedman, "Immunobiology of chronic lymphocytic leukemia," Hematol. Oncol. Clin. North Am., 4(2):405-29, Apr. 1990.
Geibler et al., "Transcriptional activators of human genes with programmable DNA-specificity," PloS One 6(5):e19509, May 2011.
GenBank Association No. CAD88204.1, "anti-human CD19 monoclonal antibody 4G7 immunoglobulin kappa light chain [Mus musculus]," Jan. 4, 2013, 2 pages.
GenBank Association No. CAD88275.1, "anti-human CD19 monoclonal antibody 4G7 immunoglobulin gammal heavy chain [Mus musculus]," Jan. 15, 2013, 2 pages.
GenBank Accession No. X02883, Human gene for T-cell receptor alpha chain C region, 2016.
GenBank Accession No. CAI77667.1, anti-human-CD28-anti-human-CD19 bi-scFv antibody fragment precursor [synthetic construct], 2005, 2 total pages.
GenBank Accession No. AAK72403.1, mutant CD8 alpha antigen [Homo sapiens], 2001, 1 total page.
Giusti et al., Proc. Natl. Acad. Sci. USA. May 1987; 84 (9): 2926-2930.
Glass et al., "The National Cancer Data Base report on non-Hodgkin's lymphoma," Cancer, 80(12):2311-20, Dec. 1997.
Goodman et al., "New perspectives on the approach to chronic lymphocytic leukemia," Leukemia and Lymphoma 22(1-2):1, Jan. 1996.
Greenberg, "Adoptive T cell therapy of tumors: mechanisms operative in the recognition and elimination of tumor cells," Adv. Immunol., 49:281-355, Jan. 1991.
Greenwald, R.J. et al. (2002). "Negative co-receptors on lymphocytes," Curr. Opin. Immunol. 14:391-396.
Gussow et al., Methods in Enzymology. 1991; 203: 99-121.
Hale et al., Improving the outcome of bone marrow transplantation by using CD52 monoclonal antibodies to prevent graft-versus-host disease and graft rejection, Blood. Dec. 15, 1998;92(12):4581-90.
Hedrick et al., "Chimeric T cell receptor-immunoglobulin molecules: function and applications," Int. Rev. Immunol., 10(2-3):279-80, Jan. 1993.
Helen E Heslop: "Safer Cars", Molecular Therapy, vol. 18, No. 4, Apr. 1, 2010, XP55609534.
Henkart, "CTL effector functions," Semin. Immunol., 9(2):85-6, Apr. 1997.
Heslop et al., "Long-term restoration of immunity against Epstein-Barr virus infection by adoptive transfer of gene-modified virus-specific T lymphocytes," Nat. Med., 2(5):551-5, May 1996.
Hockemeyer et al. (2011). "Genetic engineering of human pluripotent cells using TALE nucleases," Nature Biotechnol. 29:731-734.
Hofmann. M. et al. (2012). "Generation, selection and preclinical characterization of an Fc-optimized FLT3 antibody for the treatment of myeloid leukemia." Leukemia 26:1228-1237.
Holm et al., Mol. Immunol. Feb. 2007; 44 (6): 1075-1084.
Howard et al., "CD3zeta subunit can substitute for the gamma subunit of $Fc_E$ receptor type I in assembly and functional expression of the high-affinity IgE receptor: Evidence for interreceptor complementation," Proc. Natl. Acad. Sci. US.A, 87(18): 7015-9, Sep. 1990.
Huang et al., "Heritable gene targeting in zebrafish using customized TALENs," Nat. Biotechnol., 29(8):699-700, Aug. 2011.
Hudecek et al., Clin. Cancer Res. Jun. 15, 2013; 19 (12): 3153-64.
Humbert et al., Targeted Gene Therapies: Tools, Applications, Optimization, Grit Rev Biochem Mol Biol. May 2012; 47(3): 264-281.
Huye et al., Combining mTor inhibitors with rapamycin-resistant T cells: a two-pronged approach to tumor elimination, Mol Ther. Dec. 2011;19(12):2239-48.
Imai, C. et al. (2004). Leukemia 18:676-684.
International Search Report dated Jul. 30, 2014, for PCT Application No. PCT/EP2014/059662, filed on May 12, 2014, 5 pages.

International Search Report dated Aug. 13, 2014, for PCT Application No. PCT/IB2014/061409, filed on May 13, 2014, 4 pages.
International Search Report dated Sep. 15, 2014, for PCT Application No. PCT/IB2014/061412, filed on May 13, 2014, 5 pages.
International Search Report dated Jul. 25, 2013, for PCT Application No. PCT/US2013/040755, filed on May 13, 2013, 6 pages.
Jaeger, L. (1990). Clinical Immunology and Allergology, vol. 1, pp. 219-222, 11 total pages (with English translation).
Jena et al. PloS One. 2013; 8 (3): e57838; pp. 1-12.
Jena et al., "Redirecting T-cell specificity by introducing a tumor-specific chimeric antigen receptor," Blood, 116(7):1035-44, Aug. 2010.
Jinek et al., "A programmable dual-RNA-guided DNA endonuclease in adaptive bacterial immunity," Science, 337(6096):816-21, Jun. 2012.
Jun., C.H. (2007). "Adoptive T cell therapy for cancer in the clinic," J. Clin. Invest. 117:1466-1476.
Kabat et al., "Sequences of proteins of immunological interest," DIANE publishing, 101-129, 1991.
Kalish and Glazer, "Targeted genome modification via triple helix formation," Ann. N.Y. Acad. Sci., 1058(1):151-61, Nov. 2005.
Kariko et al., Incorporation of Pseudouridine Into mRNA Yields Superior Nonimmunogenic Vector With Increased Translational Capacity and Biological Stability, Mol Ther. Nov. 2008; 16(11): 1833-1840.
Kebriaei et al., "Chimeric antibody receptors (CARs): driving T-cell specificity to enhance anti-tumor immunity," Frontiers in bioscience, Jan. 1, 2012, 4: 520-531.
Kebriaei et al., "Infusing CD19-Directed T Cells to Augment Disease Control in Patients Undergoing Autologous Hematopietic Stem-Cell Transplantation for Advanced B-Lymphoid Malignancies," Human Gene Therapy, May 1, 2012, pp. 444-450, vol. 23, No. 5.
Keichiro Mihara et al: "Synergistic and persistent effect of T-cell immunotherapy with anti-CD19 or anti-CD38 chimeric receptor in conjunction with rituximab on B-cell non-Hodgkin lymphoma", British Journal of Haematology, vol. 151, No. 1, 1 Oct. 2010, pp. 37-46.
Kim, K-D. et al. (2009). "Synergistic inhibition of T-cell activation by a cell-permeable ZAP-70 mutant and ctCTLA-4," Biochem. Biophys. Res. Commun. 381:355-360.
Kim, J.G. et al. (2007). "Alemtuzumab plus CHOP as front-line chemotherapy for patients with peripheral T-cell lymphomas: A phase II study," Cancer Chemotherapy and Pharmacology 60:129-134.
Kugler et al. (Protein Eng. Des. Sel. Mar. 2009; 22 (3): 135-47.
Li et al., "TAL nucleases (TALNs): hybrid proteins composed of TAL effectors and Fokl DNA-cleavage domain," Nucleic. Acids. Res., 39(1):359-72, Jan. 2011.
Lipowska-Bhalla et al., "Targeted immunotherapy of cancer with CAR T cells: achievements and challenges," Cancer Immunology, Immunotherapy, Springer, Apr. 22, 2012, pp. 953-962, vol. 61, No. 7, Berlin, DE.
Liu et al., "Inhibition of T cell signaling by immunophilin-ligand complexes correlates with loss of calcineurin phosphatase activity," Biochemistry 31(16):3896-901, Apr. 1992.
Maccallum et al. (J. Mol. Biol. Oct. 11, 1996; 262 (5): 732-745.
Mahfouz, M.M. et al. (2011). "De Novo-engineered transcription activator-like effector (TALE) hybrid nuclease with novel DNA binding specificity creates double-strand breaks," PNAS 108:2623-2628.
Mali et al., "RNA-guided human genome engineering via Cas9," Science, 339(6121):823-6, Feb. 2013.
Mariuzza et al. (Annu. Rev. Biophys. Biophys. Chem. 1987; 16: 139-159.
Meeker et al. (1984). "A unique human B lymphocyte antigen defined by a monoclonal antibody," Hybridoma. 1984 Winter; 3 (4): 305-20.
Miller, J.C. et al. (2011). "A TALE nuclease architecture for efficient genome editing," Nat. Biotechnol. 29:143-148.
Milone et al., Mol. Ther. Aug. 2009; 17 (8): 1453-64.

(56) References Cited

OTHER PUBLICATIONS

Mizoguchi, A. et al. (1998). "Pathogenic role of IL-4 but not IFN-gamma in colitis of TCRalpha knockout mice," Gastroenterology 114:A1041.
Mockey et al., mRNA transfection of dendritic cells: Synergistic effect of ARCA mRNA capping with Poly(A) chains in cis and in trans for a high protein expression level, Biochemical and Biophysical Research Communications 340 (2006) 1062-1068.
Moscou et al. "A simple cipher governs DNA recognition by TAL effectors," Science, 326(5959):1501, Dec. 2009.
Noris, M. et al. (2007). "Regulatory T cells and T cell depletion: Role of immunosuppressive drugs," J. Am. Soc. Nephrol. 18:1007-1018.
Non-Final Office Action dated Jan. 27, 2021, for U.S. Appl. No. 17/099,608, filed Nov. 16, 2020, 7 pages.
Notice of Allowance dated Aug. 25, 2020, for U.S. Appl. No. 14/891,296, filed Nov. 13, 2015, 12 pages.
Osterborg, A. et al. (1997). "Clonal CD8+ and CD52-T cells are induced in responding B cell lymphoma patients treated with campath-1 H (anti CD52)," European J. Haematology 58:5-13.
Paques et al. "Meganucleases and DNA double-strand break-induced recombination: perspectives for gene therapy," Curr. Gene Ther., 7(1):49-66, Feb. 2007.
Park et al., "Treating cancer with genetically engineered T cells," Trends Biotechnol., 29(11):550-7, Nov. 2011.
Peipp, M. et al: "Efficient eukaryotic expression of fluorescent scFv fusion proteins directed against CD antigens for FACS applications," J. Immunological Methods 285:265-280.
Perrin et al., "Asymmetrical recognition and activity of the I-SceI endonuclease on its site and on intron-exon junctions," Embo. J., 12(7):2939-47, Jul. 1993.
Pingoud et al. "Precision genome surgery," Nat. Biotechnol., 25(7):743-4, Jul. 2007.
Poirot et al Multiplex genome-edited T-cell manufacturing platform for "Off-the-Shelf" adoptive T-cell immunotherapies. Can. Res. 75:3853-3864, 2015.
Porteus and Carroll, "Gene targeting using zinc finger nucleases," Nat. Biotechnol., 23(8):967-73, Aug. 2005.
Qasim et al., Molecular remission of infant B-ALL after infusion of universal TALEN gene-edited CAR T cells, Sci. Transl. Med. 9, eaaj2013 (2017) Jan. 25, 2017, 1-8.
Ramiro et al., Differential Developmental Regulation and Functional Effects on Pre-TCR Surface Expression of Human pT$\alpha^a$ and pT$\alpha^b$ Spliced Isoforms, J. Immunol. (2001) vol. 167, pp. 5106-5114.
Riddell et al., "Restoration of viral immunity in immunodeficient humans by the adoptive transfer of T cell clones," Science, 257(5067):238-41, Jul. 1992.
Rieux-Laucat et al. (N. Engl. J. Med. May 4, 2006; 354 (18): 1913-21.
Robbins et al., "Human tumor antigens recognized by T cells," Curr. Opin. Immunol., 8(5):628-36, Oct. 1996.
Roberts et al., "Targeting of human immunodeficiency virus-infected cells by CD8+ T lymphocytes armed with universal T-cell receptors," Blood, 84(9):2878-89, Nov. 1994.
Rodgers et al., Regulated α-globin mRNA decay is a cytoplasmic event proceeding through 3'-to-5' exosome-dependent decapping, RNA (2002), 8:1526-1537.
Rouet et al., "Introduction of double-strand breaks into the genome of mouse cells by expression of a rare-cutting endonuclease," Mol. Cell Biol., 14(12):8096-106, Dec. 1994.
Rudikoff et al. (Proc. Natl. Acad. Sci. USA. 1982; 79: 1979-1983.
Sample (2015). Baby girl is the first in the world to be treated with 'designer immune cells,' The Guardian, 3 total pages.
Sanchez et al., "Signal transduction by immunoglobulin is mediated through Ig alpha and Ig beta," J. Exp. Med., 178(3): 1049-1055, Sep. 1993.
Scheuermann et al., "CD19 antigen in leukemia and lymphoma diagnosis and immunotherapy," Leuk. Lymphoma., 18(5-6):385-397, Aug. 1995.
Shipp et al., Cancer: Principles and Practice of Oncology, Lippincott-Raven Publishers, Philadelphia, p. 2165-2190, 1997.
Sorek et al., "CRISPR-mediated adaptive immune systems in bacteria and archaea," Annu. Rev. Biochem., Jun. 2013.
Stoddard, "Horning endonuclease structure and function," Q. Rev. Biophys., 38(1):49-95, Feb. 2005.
Tang et al. (BMJ Open. Dec. 30, 2016; 6 (12): e013904; pp. 1-7.
Tanguay et al. (1996). "Translational Efficiency Is Regulated by the Length of the 3' Untranslated Region," Mol. Cell. Biol. 16:146-156.
Torikai, H. et al. (2012). "A foundation for universal T-cell based immunotherapy: T-cells engineered to express a CD19-specific chimeric-antigen-receptor and eliminate expression of endogenous TCR," Blood 119:5597-5706.
Trop et al., Competitive Displacement of pTα by TCR-α During TCR Assembly Prevents Surface Coexpression of Pre-TCR and αβ TCR1, The Journal of Immunology, 2000, 165: 5566-5572.
Uckun et al., "Detailed studies on expression and function of CD19 surface determinant by using B43 monoclonal antibody and the clinical potential of anti-CD19 immunotoxins," Blood, 71(1):13-29, Jan. 1988.
Vajdos et al. (J. Mol. Biol. 2002 Jul 5; 320 (2): 415-428.
Valton, J. et al. (2015). "A Multidrug-resistant engineered CAR T Cell for allogeneic combination Immunotherapy," Mol. Ther. 23:1507-1518.
van der Stegen et al. (Nat. Rev. Drug Discov. Jul. 2015; 14 (7): 499-509.
Verado et al., Regulatory sequences in the 3' Untranslated region of the human cGMP-Phosphodiesterase Ji-Subunit gene, Invest Ophthalmol Vis Sci. Jun. 2009 ; 50(6): 2591-2598.
Walter et al., "Reconstitution of cellular immunity against cytomegalovirus in recipients of allogeneic bone marrow by transfer of T-cell clones from the donor," N. Engl. J. Med., 333(16): 1038-44, Oct. 1995.
Weiss et al., "Signal transduction by the T cell antigen receptor," Semin. Immunol., 3(5):313-24, Sep. 1991.
WHO (2001). International nonproprietary names for pharmaceutical substances (INN). WHO Drug Information, vol. 15, No. 1, 26 total pages.
Winkler et al. J. Immunol. Oct. 15, 2000; 165 (8): 4505-4514.
Wood et al. (2011). "Targeted genome editing across species using ZFNs and TALENs," Science 333:307.
Written Opinion of the International Searching Authority dated Jul. 30, 2014, for PCT Application No. PCT/EP2014/059662, filed on May 12, 2014, 6 pages.
Written Opinion of the International Searching Authority dated Aug. 13, 2014, for PCT Application No. PCT/IB2014/061409, filed on May 13, 2014, 6 pages.
Written Opinion of the International Searching Authority dated Sep. 15, 2014, for PCT Application No. PCT/IB2014/061412, filed on May 13, 2014, 7 pages.
Written Opinion of the International Searching Authority dated Jul. 25, 2013, for PCT Application No. PCT/US2013/040755.
Wu et al. J. Mol. Biol. Nov. 19, 1999; 294 (1): 151-162.
Yamaguchi et al. (2008). Cd52, known as a major maturation-associated sperm membrane antigen secreted from the epididymis, is not required for fertilization in the mouse, Genes to Cells 13:851-861.
Yee et al., "Isolation of tyrosinase-specific CD8+ and CD4+ T cell clones from the peripheral blood of melanoma patients following in vitro stimulation with recombinant vaccinia virus," J. Immunol., 157(9):4079-86, Nov. 1996.
Yu, C-M. et al. (2012). "Rationalization and design of the complementarity determining region sequences in an antibody-antigen recognition interface," PLoS One 7:e33340.
Zhong, X-S. et al. (2010). "Chimeric antigen receptors combining 4-IBB and CD28 signaling domains augment Plakinase/AKT/Bcl-X$_L$ activation and CD8+ t cell-mediated tumor eradication," Mol. Therapy 18:413-420.

\* cited by examiner

SEQUENCE LISTING

<160> NUMBER OF SEQ ID NOS: 24

<210> SEQ ID NO 1
<211> LENGTH: 464
<212> TYPE: PRT
<213> ORGANISM: Mus musculus
<220> FEATURE:
<221> NAME/KEY: MISC_FEATURE
<222> LOCATION: (1)..(464)
<223> OTHER INFORMATION: anti-human CD19 monoclonal antibody 4G7
      immunoglobulin gamma1 heavy chain

<400> SEQUENCE: 1

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Ile Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Gly Thr Tyr Tyr Gly Ser Arg Val Phe Asp
        115                 120                 125

Tyr Trp Gly Gln Gly Thr Thr Leu Thr Val Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Thr Trp Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr

```
              340                 345                 350
Ile Ser Lys Thr Lys Gly Arg Pro Lys Ala Pro Gln Val Tyr Thr Ile
            355                 360                 365
Pro Pro Pro Lys Glu Gln Met Ala Lys Asp Lys Val Ser Leu Thr Cys
        370                 375                 380
Met Ile Thr Asp Phe Phe Pro Glu Asp Ile Thr Val Glu Trp Gln Trp
385                 390                 395                 400
Asn Gly Gln Pro Ala Glu Asn Tyr Lys Asn Thr Gln Pro Ile Met Asp
                405                 410                 415
Thr Asp Gly Ser Tyr Phe Val Tyr Ser Lys Leu Asn Val Gln Lys Ser
            420                 425                 430
Asn Trp Glu Ala Gly Asn Thr Phe Thr Cys Ser Val Leu His Glu Gly
        435                 440                 445
Leu His Asn His His Thr Glu Lys Ser Leu Ser His Ser Pro Gly Lys
    450                 455                 460
```

<210> SEQ ID NO 2
<211> LENGTH: 239
<212> TYPE: PRT
<213> ORGANISM: Mus musculus
<220> FEATURE:
<221> NAME/KEY: MISC_FEATURE
<222> LOCATION: (1)..(239)
<223> OTHER INFORMATION: anti-human CD19 monoclonal antibody 4G7
      immunoglobulin kappa light chain

<400> SEQUENCE: 2

```
Met Arg Cys Leu Ala Glu Phe Leu Gly Leu Leu Val Leu Trp Ile Pro
1               5                   10                  15
Gly Ala Ile Gly Asp Ile Val Met Thr Gln Ala Ala Pro Ser Ile Pro
            20                  25                  30
Val Thr Pro Gly Glu Ser Val Ser Ile Ser Cys Arg Ser Ser Lys Ser
        35                  40                  45
Leu Leu Asn Ser Asn Gly Asn Thr Tyr Leu Tyr Trp Phe Leu Gln Arg
    50                  55                  60
Pro Gly Gln Ser Pro Gln Leu Leu Ile Tyr Arg Met Ser Asn Leu Ala
65                  70                  75                  80
Ser Gly Val Pro Asp Arg Phe Ser Gly Ser Gly Ser Gly Thr Ala Phe
                85                  90                  95
Thr Leu Arg Ile Ser Arg Val Glu Ala Glu Asp Val Gly Val Tyr Tyr
            100                 105                 110
Cys Met Gln His Leu Glu Tyr Pro Phe Thr Phe Gly Ala Gly Thr Lys
        115                 120                 125
Leu Glu Leu Lys Arg Ala Asp Ala Ala Pro Thr Val Ser Ile Phe Pro
    130                 135                 140
Pro Ser Ser Glu Gln Leu Thr Ser Gly Gly Ala Ser Val Val Cys Phe
145                 150                 155                 160
Leu Asn Asn Phe Tyr Pro Lys Asp Ile Asn Val Lys Trp Lys Ile Asp
                165                 170                 175
Gly Ser Glu Arg Gln Asn Gly Val Leu Asn Ser Trp Thr Asp Gln Asp
            180                 185                 190
Ser Lys Asp Ser Thr Tyr Ser Met Ser Ser Thr Leu Thr Leu Thr Lys
        195                 200                 205
Asp Glu Tyr Glu Arg His Asn Ser Tyr Thr Cys Glu Ala Thr His Lys
    210                 215                 220
Thr Ser Thr Ser Pro Ile Val Lys Ser Phe Asn Arg Asn Glu Cys
```

```
225                 230                 235
```

<210> SEQ ID NO 3
<211> LENGTH: 121
<212> TYPE: PRT
<213> ORGANISM: Mus musculus
<220> FEATURE:
<221> NAME/KEY: MISC_FEATURE
<222> LOCATION: (1)..(121)
<223> OTHER INFORMATION: fragment of anti-human CD19 monoclonal antibody
      4G7 immunoglobulin gamma1 heavy chain-(residues 20-140)

<400> SEQUENCE: 3

```
Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser
        115                 120
```

<210> SEQ ID NO 4
<211> LENGTH: 115
<212> TYPE: PRT
<213> ORGANISM: Mus musculus
<220> FEATURE:
<221> NAME/KEY: MISC_FEATURE
<222> LOCATION: (1)..(115)
<223> OTHER INFORMATION: fragment of anti-human CD19 monoclonal antibody
      4G7 immunoglobulin kappa light chain (residues 21-130)

<400> SEQUENCE: 4

```
Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ala Asp
        115
```

<210> SEQ ID NO 5
<211> LENGTH: 116

```
<212> TYPE: PRT
<213> ORGANISM: Artificial Sequence
<220> FEATURE:
<223> OTHER INFORMATION: fragment of anti-human CD19 monoclonal antibody
      4G7 immunoglobulin kappa light chain

<400> SEQUENCE: 5

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Ser Asp Pro
            115

<210> SEQ ID NO 6
<211> LENGTH: 15
<212> TYPE: PRT
<213> ORGANISM: Artificial Sequence
<220> FEATURE:
<223> OTHER INFORMATION: synthetic oligopeptide linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 252
<212> TYPE: PRT
<213> ORGANISM: Artificial Sequence
<220> FEATURE:
<223> OTHER INFORMATION: synthetic polypeptide scFV 4G7 version 1

<400> SEQUENCE: 7

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Gly Gly Gly Gly Ser Gly Gly
        115                 120                 125
```

```
Gly Gly Ser Gly Gly Gly Ser Asp Ile Val Met Thr Gln Ala Ala
        130             135                 140

Pro Ser Ile Pro Val Thr Pro Gly Glu Ser Val Ser Ile Ser Cys Arg
145                 150                 155                 160

Ser Ser Lys Ser Leu Leu Asn Ser Asn Gly Asn Thr Tyr Leu Tyr Trp
                165                 170                 175

Phe Leu Gln Arg Pro Gly Gln Ser Pro Gln Leu Leu Ile Tyr Arg Met
                180                 185                 190

Ser Asn Leu Ala Ser Gly Val Pro Asp Arg Phe Ser Gly Ser Gly Ser
                195                 200                 205

Gly Thr Ala Phe Thr Leu Arg Ile Ser Arg Val Glu Ala Glu Asp Val
            210                 215                 220

Gly Val Tyr Tyr Cys Met Gln His Leu Glu Tyr Pro Phe Thr Phe Gly
225                 230                 235                 240

Ala Gly Thr Lys Leu Glu Leu Lys Arg Ser Asp Pro
                245                 250
```

<210> SEQ ID NO 8
<211> LENGTH: 251
<212> TYPE: PRT
<213> ORGANISM: Artificial Sequence
<220> FEATURE:
<223> OTHER INFORMATION: synthetic polypeptide scFV 4G7 version 2

<400> SEQUENCE: 8

```
Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
                100                 105                 110

Gln Gly Thr Thr Leu Thr Val Ser Ser Gly Gly Gly Ser Gly Gly
            115                 120                 125

Gly Gly Ser Gly Gly Gly Ser Asp Ile Val Met Thr Gln Ala Ala
        130             135                 140

Pro Ser Ile Pro Val Thr Pro Gly Glu Ser Val Ser Ile Ser Cys Arg
145                 150                 155                 160

Ser Ser Lys Ser Leu Leu Asn Ser Asn Gly Asn Thr Tyr Leu Tyr Trp
                165                 170                 175

Phe Leu Gln Arg Pro Gly Gln Ser Pro Gln Leu Leu Ile Tyr Arg Met
                180                 185                 190

Ser Asn Leu Ala Ser Gly Val Pro Asp Arg Phe Ser Gly Ser Gly Ser
                195                 200                 205

Gly Thr Ala Phe Thr Leu Arg Ile Ser Arg Val Glu Ala Glu Asp Val
            210                 215                 220

Gly Val Tyr Tyr Cys Met Gln His Leu Glu Tyr Pro Phe Thr Phe Gly
225                 230                 235                 240
```

```
Ala Gly Thr Lys Leu Glu Leu Lys Arg Ala Asp
            245                 250
```

```
<210> SEQ ID NO 9
<211> LENGTH: 250
<212> TYPE: PRT
<213> ORGANISM: Artificial Sequence
<220> FEATURE:
<223> OTHER INFORMATION: synthetic polypeptide scFV FMC63

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Lys Ala Gly Gly Gly
            100                 105                 110

Gly Ser Gly Gly Gly Gly Ser Gly Gly Gly Gly Ser Gly Gly Gly Gly
        115                 120                 125

Ser Glu Val Lys Leu Gln Glu Ser Gly Pro Gly Leu Val Ala Pro Ser
130                 135                 140

Gln Ser Leu Ser Val Thr Cys Thr Val Ser Gly Val Ser Leu Pro Asp
145                 150                 155                 160

Tyr Gly Val Ser Trp Ile Arg Gln Pro Pro Arg Lys Gly Leu Glu Trp
                165                 170                 175

Leu Gly Val Ile Trp Gly Ser Glu Thr Thr Tyr Tyr Asn Ser Ala Leu
            180                 185                 190

Lys Ser Arg Leu Thr Ile Ile Lys Asp Asn Ser Lys Ser Gln Val Phe
        195                 200                 205

Leu Lys Met Asn Ser Leu Gln Thr Asp Thr Ala Ile Tyr Tyr Cys
    210                 215                 220

Ala Lys His Tyr Tyr Tyr Gly Gly Ser Tyr Ala Met Asp Tyr Trp Gly
225                 230                 235                 240

Gln Gly Thr Ser Val Thr Val Ser Ser Asp
            245                 250
```

```
<210> SEQ ID NO 10
<211> LENGTH: 112
<212> TYPE: PRT
<213> ORGANISM: Homo sapiens
<220> FEATURE:
<221> NAME/KEY: MISC_FEATURE
<222> LOCATION: (1)..(112)
<223> OTHER INFORMATION: fragment of T-cell surface glycoprotein CD3
      zeta chain

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30
```

```
Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110
```

<210> SEQ ID NO 11
<211> LENGTH: 42
<212> TYPE: PRT
<213> ORGANISM: Homo sapiens
<220> FEATURE:
<221> NAME/KEY: MISC_FEATURE
<222> LOCATION: (1)..(42)
<223> OTHER INFORMATION: Fragment of 4-1BB (residues 214-255)

<400> SEQUENCE: 11

```
Lys Arg Gly Arg Lys Lys Leu Leu Tyr Ile Phe Lys Gln Pro Phe Met
 1               5                  10                  15

Arg Pro Val Gln Thr Thr Gln Glu Glu Asp Gly Cys Ser Cys Arg Phe
             20                  25                  30

Pro Glu Glu Glu Glu Gly Gly Cys Glu Leu
             35                  40
```

<210> SEQ ID NO 12
<211> LENGTH: 41
<212> TYPE: PRT
<213> ORGANISM: Homo sapiens
<220> FEATURE:
<221> NAME/KEY: MISC_FEATURE
<222> LOCATION: (1)..(41)
<223> OTHER INFORMATION: Fragment of T-cell-specific surface
      glycoprotein CD28

<400> SEQUENCE: 12

```
Arg Ser Lys Arg Ser Arg Gly Gly His Ser Asp Tyr Met Asn Met Thr
 1               5                  10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser
             35                  40
```

<210> SEQ ID NO 13
<211> LENGTH: 69
<212> TYPE: PRT
<213> ORGANISM: Homo sapiens
<220> FEATURE:
<221> NAME/KEY: MISC_FEATURE
<222> LOCATION: (1)..(69)
<223> OTHER INFORMATION: Fragment of T-cell surface glycoprotein CD8
      alpha chain isoform 1 precursor (residues 138-206)

<400> SEQUENCE: 13

```
Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
             20                  25                  30

Gly Ala Val His Thr Arg Gly Leu Asp Phe Ala Cys Asp Ile Tyr Ile
```

```
                35                  40                  45
Trp Ala Pro Leu Ala Gly Thr Cys Gly Val Leu Leu Leu Ser Leu Val
    50                  55                  60

Ile Thr Leu Tyr Cys
65

<210> SEQ ID NO 14
<211> LENGTH: 495
<212> TYPE: PRT
<213> ORGANISM: Artificial Sequence
<220> FEATURE:
<223> OTHER INFORMATION: synthetic polypeptide 4G7-CAR version 1

<400> SEQUENCE: 14

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125

Phe Asp Tyr Trp Gly Gln Gly Thr Thr Leu Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
            180                 185                 190

Thr Tyr Leu Tyr Trp Phe Leu Gln Arg Pro Gly Gln Ser Pro Gln Leu
        195                 200                 205

Leu Ile Tyr Arg Met Ser Asn Leu Ala Ser Gly Val Pro Asp Arg Phe
    210                 215                 220

Ser Gly Ser Gly Ser Gly Thr Ala Phe Thr Leu Arg Ile Ser Arg Val
225                 230                 235                 240

Glu Ala Glu Asp Val Gly Val Tyr Tyr Cys Met Gln His Leu Glu Tyr
                245                 250                 255

Pro Phe Thr Phe Gly Ala Gly Thr Lys Leu Glu Leu Lys Arg Ala Asp
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
```

```
            325                 330                 335
Ile Thr Leu Tyr Cys Lys Arg Gly Arg Lys Lys Leu Leu Tyr Ile Phe
            340                 345                 350
Lys Gln Pro Phe Met Arg Pro Val Gln Thr Thr Gln Glu Glu Asp Gly
            355                 360                 365
Cys Ser Cys Arg Phe Pro Glu Glu Glu Glu Gly Cys Glu Leu Arg
            370                 375             380
Val Lys Phe Ser Arg Ser Ala Asp Ala Pro Ala Tyr Gln Gln Gly Gln
385                 390                 395                 400
Asn Gln Leu Tyr Asn Glu Leu Asn Leu Gly Arg Arg Glu Glu Tyr Asp
                405                 410                 415
Val Leu Asp Lys Arg Arg Gly Arg Asp Pro Glu Met Gly Gly Lys Pro
                420                 425                 430
Arg Arg Lys Asn Pro Gln Glu Gly Leu Tyr Asn Glu Leu Gln Lys Asp
                435                 440                 445
Lys Met Ala Glu Ala Tyr Ser Glu Ile Gly Met Lys Gly Glu Arg Arg
            450                 455                 460
Arg Gly Lys Gly His Asp Gly Leu Tyr Gln Gly Leu Ser Thr Ala Thr
465                 470                 475                 480
Lys Asp Thr Tyr Asp Ala Leu His Met Gln Ala Leu Pro Pro Arg
                485                 490                 495

<210> SEQ ID NO 15
<211> LENGTH: 495
<212> TYPE: PRT
<213> ORGANISM: Artificial Sequence
<220> FEATURE:
<223> OTHER INFORMATION: synthetic polypeptide 4G7-CAR version 2

<400> SEQUENCE: 15

Met Glu Thr Asp Thr Leu Leu Leu Trp Val Leu Leu Leu Trp Val Pro
1               5                   10                  15
Gly Ser Thr Gly Glu Val Gln Leu Gln Gln Ser Gly Pro Glu Leu Ile
            20                  25                  30
Lys Pro Gly Ala Ser Val Lys Met Ser Cys Lys Ala Ser Gly Tyr Thr
        35                  40                  45
Phe Thr Ser Tyr Val Met His Trp Val Lys Gln Lys Pro Gly Gln Gly
    50                  55                  60
Leu Glu Trp Ile Gly Tyr Ile Asn Pro Tyr Asn Asp Gly Thr Lys Tyr
65                  70                  75                  80
Asn Glu Lys Phe Lys Gly Lys Ala Thr Leu Thr Ser Asp Lys Ser Ser
                85                  90                  95
Ser Thr Ala Tyr Met Glu Leu Ser Ser Leu Thr Ser Glu Asp Ser Ala
            100                 105                 110
Val Tyr Tyr Cys Ala Arg Gly Thr Tyr Tyr Tyr Gly Ser Arg Val Phe
        115                 120                 125
Asp Tyr Trp Gly Gln Gly Thr Thr Leu Thr Val Ser Ser Gly Gly Gly
    130                 135                 140
Gly Ser Gly Gly Gly Gly Ser Gly Gly Gly Gly Ser Asp Ile Val Met
145                 150                 155                 160
Thr Gln Ala Ala Pro Ser Ile Pro Val Thr Pro Gly Glu Ser Val Ser
                165                 170                 175
Ile Ser Cys Arg Ser Ser Lys Ser Leu Leu Asn Ser Asn Gly Asn Thr
            180                 185                 190
Tyr Leu Tyr Trp Phe Leu Gln Arg Pro Gly Gln Ser Pro Gln Leu Leu
```

```
                195                 200                 205
Ile Tyr Arg Met Ser Asn Leu Ala Ser Gly Val Pro Asp Arg Phe Ser
210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Cys Glu Leu Arg
370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 16
<211> LENGTH: 494
<212> TYPE: PRT
<213> ORGANISM: Artificial Sequence
<220> FEATURE:
<223> OTHER INFORMATION: synthetic polypeptide FMC63-CAR

<400> SEQUENCE: 16

Met Glu Thr Asp Thr Leu Leu Leu Trp Val Leu Leu Leu Trp Val Pro
1               5                   10                  15

Gly Ser Thr Gly Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
        35                  40                  45

Ile Ser Lys Tyr Leu Asn Trp Tyr Gln Gln Lys Pro Asp Gly Thr Val
    50                  55                  60

Lys Leu Leu Ile Tyr His Thr Ser Arg Leu His Ser Gly Val Pro Ser
```

```
            65                  70                  75                  80
Arg Phe Ser Gly Ser Gly Ser Gly Thr Asp Tyr Ser Leu Thr Ile Ser
                    85                  90                  95
Asn Leu Glu Gln Glu Asp Ile Ala Thr Tyr Phe Cys Gln Gln Gly Asn
                100                 105                 110
Thr Leu Pro Tyr Thr Phe Gly Gly Gly Thr Lys Leu Glu Ile Thr Lys
                115                 120                 125
Ala Gly Gly Gly Ser Gly Gly Gly Ser Gly Gly Gly Gly Ser
130                 135                 140
Gly Gly Gly Ser Glu Val Lys Leu Gln Glu Ser Gly Pro Gly Leu
145                 150                 155                 160
Val Ala Pro Ser Gln Ser Leu Ser Val Thr Cys Thr Val Ser Gly Val
                165                 170                 175
Ser Leu Pro Asp Tyr Gly Val Ser Trp Ile Arg Gln Pro Pro Arg Lys
                180                 185                 190
Gly Leu Glu Trp Leu Gly Val Ile Trp Gly Ser Glu Thr Thr Tyr Tyr
                195                 200                 205
Asn Ser Ala Leu Lys Ser Arg Leu Thr Ile Ile Lys Asp Asn Ser Lys
210                 215                 220
Ser Gln Val Phe Leu Lys Met Asn Ser Leu Gln Thr Asp Asp Thr Ala
225                 230                 235                 240
Ile Tyr Tyr Cys Ala Lys His Tyr Tyr Gly Gly Ser Tyr Ala Met
                245                 250                 255
Asp Tyr Trp Gly Gln Gly Thr Ser Val Thr Val Ser Ser Asp Pro Thr
                260                 265                 270
Thr Thr Pro Ala Pro Arg Pro Pro Thr Pro Ala Pro Thr Ile Ala Ser
            275                 280                 285
Gln Pro Leu Ser Leu Arg Pro Glu Ala Cys Arg Pro Ala Ala Gly Gly
            290                 295                 300
Ala Val His Thr Arg Gly Leu Asp Phe Ala Cys Asp Ile Tyr Ile Trp
305                 310                 315                 320
Ala Pro Leu Ala Gly Thr Cys Gly Val Leu Leu Leu Ser Leu Val Ile
                325                 330                 335
Thr Leu Tyr Cys Lys Arg Gly Arg Lys Lys Leu Leu Tyr Ile Phe Lys
                340                 345                 350
Gln Pro Phe Met Arg Pro Val Gln Thr Thr Gln Glu Glu Asp Gly Cys
            355                 360                 365
Ser Cys Arg Phe Pro Glu Glu Glu Gly Gly Cys Glu Leu Arg Val
370                 375                 380
Lys Phe Ser Arg Ser Ala Asp Ala Pro Ala Tyr Gln Gln Gly Gln Asn
385                 390                 395                 400
Gln Leu Tyr Asn Glu Leu Asn Leu Gly Arg Arg Glu Glu Tyr Asp Val
                405                 410                 415
Leu Asp Lys Arg Arg Gly Arg Asp Pro Glu Met Gly Gly Lys Pro Arg
                420                 425                 430
Arg Lys Asn Pro Gln Glu Gly Leu Tyr Asn Glu Leu Gln Lys Asp Lys
                435                 440                 445
Met Ala Glu Ala Tyr Ser Glu Ile Gly Met Lys Gly Glu Arg Arg Arg
                450                 455                 460
Gly Lys Gly His Asp Gly Leu Tyr Gln Gly Leu Ser Thr Ala Thr Lys
465                 470                 475                 480
Asp Thr Tyr Asp Ala Leu His Met Gln Ala Leu Pro Pro Arg
                485                 490
```

<210> SEQ ID NO 17
<211> LENGTH: 1488
<212> TYPE: DNA
<213> ORGANISM: Artificial Sequence
<220> FEATURE:
<223> OTHER INFORMATION: synthetic polynucleotide 4G7-CAR version 2

<400> SEQUENCE: 17

```
atggagaccg acaccctgct gctgtgggtg ctgctgctgt gggtgccagg cagcaccggc      60
gaggtgcagc tgcagcagag cggacccgag ctgatcaagc aggcgccag cgtgaagatg      120
agctgcaagg ccagcggcta caccttcacc agctacgtga tgcactgggt gaagcagaag     180
ccaggccagg gcctggagtg gatcggctac atcaacccct acaacgacgg caccaagtac    240
aacgagaagt tcaagggcaa ggccaccctg accagcgaca gagcagcag caccgcctac     300
atggagctga gcagcctgac cagcgaggac agcgccgtgt actactgcgc cagaggcacc    360
tactactacg gcgccggt gttcgactac tggggccagg gcaccaccct gaccgtgagc      420
tctggcggag gcggctctgg cggaggcggc tctggcggag gcggcagcga catcgtgatg     480
acccaggctg cccccagcat ccccgtgacc caggcgaga gcgtgagcat cagctgccgg     540
agcagcaaga gcctgctgaa cagcaacggc aacacctacc tgtactggtt cctgcagcgg     600
ccaggccaga gcccccagct gctgatctac cggatgagca acctggccag cggcgtgccc    660
gaccggttca gcggcagcgg cagcggcacc gccttcaccc tgcggatcag ccgggtggag    720
gccgaggacg tgggcgtgta ctactgcatg cagcacctgg agtacccctt caccttcgga    780
gccggcacca agctggagct gaagcggtcg gatcccacca ccaccccagc cccacggcca    840
cctacccctg ccccaaccat cgccagccag cccctgagcc tgcggcctga agcctgcagg    900
cctgccgccg gaggagccgt gcacacaagg ggcctggact tcgcctgcga catctatatc    960
tgggcccccc tggccgggac atgcggggtg ctgctgctgt ccctggtgat tacactgtat    1020
tgcaaacggg gccggaagaa gctgctgtac atcttcaagc agcccttcat gcggccgtg    1080
cagaccaccc aggaggagga cggctgcagc tgcggttcc ccgaggaaga ggaaggcggc    1140
tgcgagctgc gggtgaagtt cagccggagc gccgacgcc cagcctacca gcagggccag    1200
aaccagctgt acaacgagct gaacctggga cggcgggagg agtacgacgt gctggacaag    1260
cggcggggac gggaccccga gatgggcggc aagcctcgcc ggaagaatcc ccaggagggc    1320
ctgtacaacg agctgcagaa ggacaagatg gccgaggcct acagcgagat cggcatgaag    1380
ggcgagcggc gccggggcaa gggccacgac ggcctgtacc agggcctgag caccgccacc    1440
aaggacacct acgacgccct gcacatgcag gccctgccac cccggtga                 1488
```

<210> SEQ ID NO 18
<211> LENGTH: 20
<212> TYPE: PRT
<213> ORGANISM: Artificial Sequence
<220> FEATURE:
<223> OTHER INFORMATION: synthetic oligopeptide signal peptide

<400> SEQUENCE: 18

Met Glu Thr Asp Thr Leu Leu Leu Trp Val Leu Leu Leu Trp Val Pro
1               5                   10                  15

Gly Ser Thr Gly
            20

<210> SEQ ID NO 19

```
<211> LENGTH: 21
<212> TYPE: PRT
<213> ORGANISM: Artificial Sequence
<220> FEATURE:
<223> OTHER INFORMATION: synthetic oligopeptide signal peptide

<400> SEQUENCE: 19

Met Ala Leu Pro Val Thr Ala Leu Leu Leu Pro Leu Ala Leu Leu Leu
1               5                   10                  15

His Ala Ala Arg Pro
            20

<210> SEQ ID NO 20
<211> LENGTH: 49
<212> TYPE: PRT
<213> ORGANISM: Artificial Sequence
<220> FEATURE:
<223> OTHER INFORMATION: Synthetic oligonucleotide TRAC_T01

<400> SEQUENCE: 20

Thr Thr Gly Thr Cys Cys Cys Ala Cys Ala Gly Ala Thr Ala Thr Cys
1               5                   10                  15

Cys Ala Gly Ala Ala Cys Cys Thr Gly Ala Cys Cys Cys Thr Gly
            20                  25                  30

Cys Cys Gly Thr Gly Thr Ala Cys Cys Ala Gly Cys Thr Gly Ala Gly
        35                  40                  45

Ala

<210> SEQ ID NO 21
<211> LENGTH: 530
<212> TYPE: PRT
<213> ORGANISM: Artificial Sequence
<220> FEATURE:
<223> OTHER INFORMATION: Synthetic polypeptide Repeat TRAC_T01-L

<400> SEQUENCE: 21

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
```

```
                180                 185                 190
Gln Arg Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
            210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
            275                 280                 285

Gln Ala Leu Glu Thr Val Gln Ala Leu Leu Pro Val Leu Cys Gln Ala
            290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Val Ala Ile Ala
370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
            435                 440                 445

Val Ala Ile Ala Ser Asn Gly Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 22
<211> LENGTH: 530
<212> TYPE: PRT
<213> ORGANISM: Artificial Sequence
<220> FEATURE:
<223> OTHER INFORMATION: Synthetic polypeptide Repeat TRAC_T01-R

<400> SEQUENCE: 22

Leu Thr Pro Glu Gln Val Val Ala Ile Ala Ser His Asp Gly Gly Lys
```

```
        1               5                   10                  15
        Gln Ala Leu Glu Thr Val Gln Arg Leu Leu Pro Val Leu Cys Gln Ala
                        20                  25                  30

His Gly Leu Thr Pro Gln Gln Val Val Ala Ile Ala Ser Asn Gly Gly
                        35                  40                  45

Gly Lys Gln Ala Leu Glu Thr Val Gln Arg Leu Leu Pro Val Leu Cys
                    50                  55                  60

Gln Ala His Gly Leu Thr Pro Glu Gln Val Val Ala Ile Ala Ser His
        65                  70                  75                  80

Asp Gly Gly Lys Gln Ala Leu Glu Thr Val Gln Arg Leu Leu Pro Val
                        85                  90                  95

Leu Cys Gln Ala His Gly Leu Thr Pro Glu Gln Val Val Ala Ile Ala
                        100                 105                 110

Ser Asn Ile Gly Gly Lys Gln Ala Leu Glu Thr Val Gln Ala Leu Leu
                        115                 120                 125

Pro Val Leu Cys Gln Ala His Gly Leu Thr Pro Gln Gln Val Val Ala
                        130                 135                 140

Ile Ala Ser Asn Asn Gly Gly Lys Gln Ala Leu Glu Thr Val Gln Arg
        145                 150                 155                 160

Leu Leu Pro Val Leu Cys Gln Ala His Gly Leu Thr Pro Glu Gln Val
                        165                 170                 175

Val Ala Ile Ala Ser His Asp Gly Gly Lys Gln Ala Leu Glu Thr Val
                        180                 185                 190

Gln Arg Leu Leu Pro Val Leu Cys Gln Ala His Gly Leu Thr Pro Gln
                        195                 200                 205

Gln Val Val Ala Ile Ala Ser Asn Gly Gly Lys Gln Ala Leu Glu
                    210                 215                 220

Thr Val Gln Arg Leu Leu Pro Val Leu Cys Gln Ala His Gly Leu Thr
        225                 230                 235                 240

Pro Gln Gln Val Val Ala Ile Ala Ser Asn Asn Gly Gly Lys Gln Ala
                        245                 250                 255

Leu Glu Thr Val Gln Arg Leu Leu Pro Val Leu Cys Gln Ala His Gly
                        260                 265                 270

Leu Thr Pro Gln Gln Val Val Ala Ile Ala Ser Asn Asn Gly Gly Lys
                        275                 280                 285

Gln Ala Leu Glu Thr Val Gln Arg Leu Leu Pro Val Leu Cys Gln Ala
                        290                 295                 300

His Gly Leu Thr Pro Gln Gln Val Val Ala Ile Ala Ser Asn Gly Gly
        305                 310                 315                 320

Gly Lys Gln Ala Leu Glu Thr Val Gln Arg Leu Leu Pro Val Leu Cys
                        325                 330                 335

Gln Ala His Gly Leu Thr Pro Glu Gln Val Val Ala Ile Ala Ser Asn
                        340                 345                 350

Ile Gly Gly Lys Gln Ala Leu Glu Thr Val Gln Ala Leu Leu Pro Val
                        355                 360                 365

Leu Cys Gln Ala His Gly Leu Thr Pro Glu Gln Val Val Ala Ile Ala
                        370                 375                 380

Ser His Asp Gly Gly Lys Gln Ala Leu Glu Thr Val Gln Arg Leu Leu
        385                 390                 395                 400

Pro Val Leu Cys Gln Ala His Gly Leu Thr Pro Glu Gln Val Val Ala
                        405                 410                 415

Ile Ala Ser Asn Ile Gly Gly Lys Gln Ala Leu Glu Thr Val Gln Ala
                        420                 425                 430
```

```
Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530
```

<210> SEQ ID NO 23
<211> LENGTH: 2814
<212> TYPE: DNA
<213> ORGANISM: Artificial Sequence
<220> FEATURE:
<223> OTHER INFORMATION: Synthetic polynucleotide TRAC_T01-R TALEN

<400> SEQUENCE: 23

```
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
agaggtccac cgttacagtt ggacacaggc caacttctca agattgcaaa acgtggcggc   420
gtgaccgcag tggaggcagt gcatgcatgg cgcaatgcac tgacgggtgc cccgctcaac   480
ttgacccccc agcaggtggt ggccatcgcc agcaatggcg gtggcaagca ggcgctggag   540
acggtccagc ggctgttgcc ggtgctgtgc caggcccacg gcttgacccc ccagcaggtg   600
gtggccatcg ccagcaataa tggtggcaag caggcgctgg agacggtcca gcggctgttg   660
ccggtgctgt gccaggccca cggcttgacc ccccagcagg tggtggccat cgccagcaat   720
ggcggtggca agcaggcgct ggagacggtc agcggctgt tgccggtgct gtgccaggcc   780
cacggcttga ccccggagca ggtggtggcc atcgccagcc acgatggcgg caagcaggcg   840
ctggagacgg tccagcggct gttgccggtg ctgtgccagg cccacggctt gaccccggag   900
caggtggtgg ccatcgccag ccacgatggc ggcaagcagg cgctggagac ggtccagcgg   960
ctgttgccgg tgctgtgcca ggcccacggc ttgaccccgg agcaggtggt ggccatcgcc  1020
agccacgatg gcggcaagca ggcgctggag acggtccagc ggctgttgcc ggtgctgtgc  1080
caggcccacg gcttgacccc ggagcaggtg gtggccatcg ccagcaatat tggtggcaag  1140
caggcgctgg agacggtgca ggcgctgttg ccggtgctgt gccaggccca cggcttgacc  1200
ccggagcagg tggtggccat cgccagccac gatggcggca agcaggcgct ggagacggtc  1260
cagcggctgt tgccggtgct gtgccaggcc cacggcttga ccccggagca ggtggtggcc  1320
atcgccagca atattggtgg caagcaggcg ctggagacgg tgcaggcgct gttgccggtg  1380
ctgtgccagg cccacggctt gaccccccag caggtggtgg ccatcgccag caataatggt  1440
```

```
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt gccggtgct gtgccaggcc     1800 cacggcttga ccccccagca ggtggtggcc atcgccagca atggcggtgg caagcaggcg    1860
ctggagacgt ccagcggct gttgccggtg ctgtgccagg cccacggctt gaccccggag     1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg gctcccca tcgactacgg cgtgatcgtg       2460
gacaccaagg cctactccgg cggctacaac ctgcccatcg ccaggccga cgaaatgcag     2520 aggtacgtgg aggagaacca gaccaggaac aagcacatca ccccaacga gtggtggaag     2580 gtgtacccct ccagcgtgac cgagttcaag ttcctgttcg tgtccggcca cttcaagggc    2640
aactacaagg cccagctgac caggctgaac cacatcacca ctgcaacgg cgccgtgctg     2700 tccgtggagg agctcctgat cggcggcgag atgatcaagg ccggcaccct gacctggag     2760 gaggtgagga ggaagttcaa caacggcgag atcaacttcg cggccgactg ataa          2814
```

<210> SEQ ID NO 24
<211> LENGTH: 2832
<212> TYPE: DNA
<213> ORGANISM: Artificial Sequence
<220> FEATURE:
<223> OTHER INFORMATION: Synthetic polynucleotide

<400> SEQUENCE: 24

```
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccc tcgctgtcaa gtatcaggac atgatcgcag cgttgccaga ggcgacacac    300
gaagcgatcg ttggcgtcgg caaacagtgg tccggcgcac gcgctctgga ggccttgctc    360
acggtggcgg agagttgag aggtccaccg ttacagttgg acacaggcca acttctcaag    420
attgcaaaac gtgcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600 ttgaccccc agcaggtggt ggccatcgcc agcaatggcg gtggcaagca ggcgctggag    660
```

```
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgaccccc agcaggtggt ggccatcgcc   1140
agcaatggcg gtggcaagca ggcgctggag acggtccagc ggctgttgcc ggtgctgtgc   1200
caggcccacg gcttgacccc cagcaggtg tggccatcg ccagcaataa tggtggcaag   1260
caggcgctgg agacggtcca gcggctgttg ccggtgctgt gccaggccca cggcttgacc   1320
ccccagcagg tggtggccat cgccagcaat aatggtggca agcaggcgct ggagacggtc   1380
cagcggctgt tgccggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtcaggcg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccggagcagg tggtggccat cgccagccac   1860
gatggcggca agcaggcgct ggagacggtc agcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga aatccgagtt gaggcacaag   2280
ctgaagtacg tgccccacga gtacatcgag ctgatcgaga tcgcccggaa cagcaccccag   2340 gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760 ggcacctga ccctggagga ggtgaggagg aagttcaaca acggcgagat caacttcgcg   2820
gccgactgat aa                                                       2832
```

CD19 SPECIFIC CHIMERIC ANTIGEN RECEPTOR AND USES THEREOF

CROSS-REFERENCE TO RELATED APPLICATIONS

This application is a continuation of U.S. application Ser. No. 14/891,296, filed Nov. 13, 2015, now issued as U.S. Pat. No. 10,874,693, which is a National Stage entry of International Application No. PCT/EP2014/059662, filed May 12, 2014, which claims benefit of U.S. Provisional Application No. 61/888,259, filed Oct. 8, 2013, and which is a continuation-in-part of U.S. patent application Ser. No. 13/892,805, filed May 13, 2013, a continuation-in-part of International Application No. PCT/US2013/040755, filed May 13, 2013, and a continuation-in-part of International Application No. PCT/US2013/040766, filed May 13, 2013. The disclosures of the prior applications are hereby incorporated by reference in their entireties.

SEQUENCE LISTING

The Sequence Listing associated with this application is provided in text format in lieu of a paper copy, and is hereby incorporated by reference into the specification. The name of the text file containing the Sequence Listing is ALGN_017_05US_SeqList_ST25.txt. The text file is ~52.6 kilobytes, was created on Nov. 13, 2020, and is being submitted electronically via EFS-Web.

FIELD OF THE INVENTION

The present invention relates to chimeric antigen receptors (CAR). CARs are able to redirect immune cell specificity and reactivity toward a selected target exploiting the ligand-binding domain properties. In particular, the present invention relates to a Chimeric Antigen Receptor in which extracellular ligand binding is a scFV derived from a CD19 monoclonal antibody, preferably 4G7. The present invention also relates to polynucleotides, vectors encoding said CAR and isolated cells expressing said CAR at their surface. The present invention also relates to methods for engineering immune cells expressing 4G7-CAR at their surface which confers a prolonged "activated" state on the transduced cell. The present invention is particularly useful for the treatment of B-cells lymphomas and leukemia.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

CD19 is an attractive target for immunotherapy because the vast majority of B-acute lymphoblastic leukemia (B-ALL) uniformly express CD19, whereas expression is absent on non hematopoietic cells, as well as myeloid, erythroid, and T cells, and bone marrow stem cells. Clinical trials targeting CD19 on B-cell malignancies are underway with encouraging anti-tumor responses. Most infuse T cells genetically modified to express a chimeric antigen receptor (CAR) with specificity derived from the scFv region of a CD19-specific mouse monoclonal antibody FMC63 (Nicholson, Lenton et al. 1997; Cooper, Topp et al. 2003; Cooper, Jena et al. 2012) (International application: WO2013/126712). However, there is still a need to improve construction of CARs that show better compatibility with T-cell proliferation, in order to allow the cells expressing such CARs to reach significant clinical advantage.

SUMMARY OF THE INVENTION

The inventors have generated a CD19 specific CAR (4G7-CAR) comprising a scFV derived from the CD19 specific monoclonal antibody, 4G7, and have surprisingly found that introduction of the resulting 4G7-CAR into primary T cells could confer a prolonged "activated" state on the transduced cell independently of antigen binding. Following non-specific activation in vitro (e.g. with anti CD3/CD28 coated beads and recombinant IL2), these cells displayed an increased cell size (blast formation) as well as the expression of activation markers (CD25) over an extended time period compared to cells transduced with a similar CAR comprising the FMC63 scFV. This long-term activation permits extended proliferation and provides an antigen-independent mechanism for expansion of 4G7-CAR cells in vitro.

The present invention thus provides a chimeric antigen receptor comprising at least one extracellular ligand binding domain, a transmembrane domain and at least one signal transducing domain, wherein said extracellular ligand binding domain comprises a scFV derived from specific monoclonal antibody, 4G7. In particular, the CAR of the present invention once transduced into an immune cell contributes to antigen independent activation and proliferation of the cell. The present invention also relates to nucleic acid, vectors encoding the CAR comprising a scFV derived from the CD19 specific monoclonal antibody 4G7 and methods of engineering immune cells comprising introducing into said cell the 4G7 CAR. The present invention also relates to genetically modified immune cells expressing at their surface the 4G7, particularly immune cells which proliferate independently of antigen mechanism. The genetically modified immune cells of the present invention are particularly useful for therapeutic applications such as B-cell lymphoma or leukemia treatments.

DETAILED DESCRIPTION OF THE INVENTION

Figure 1:
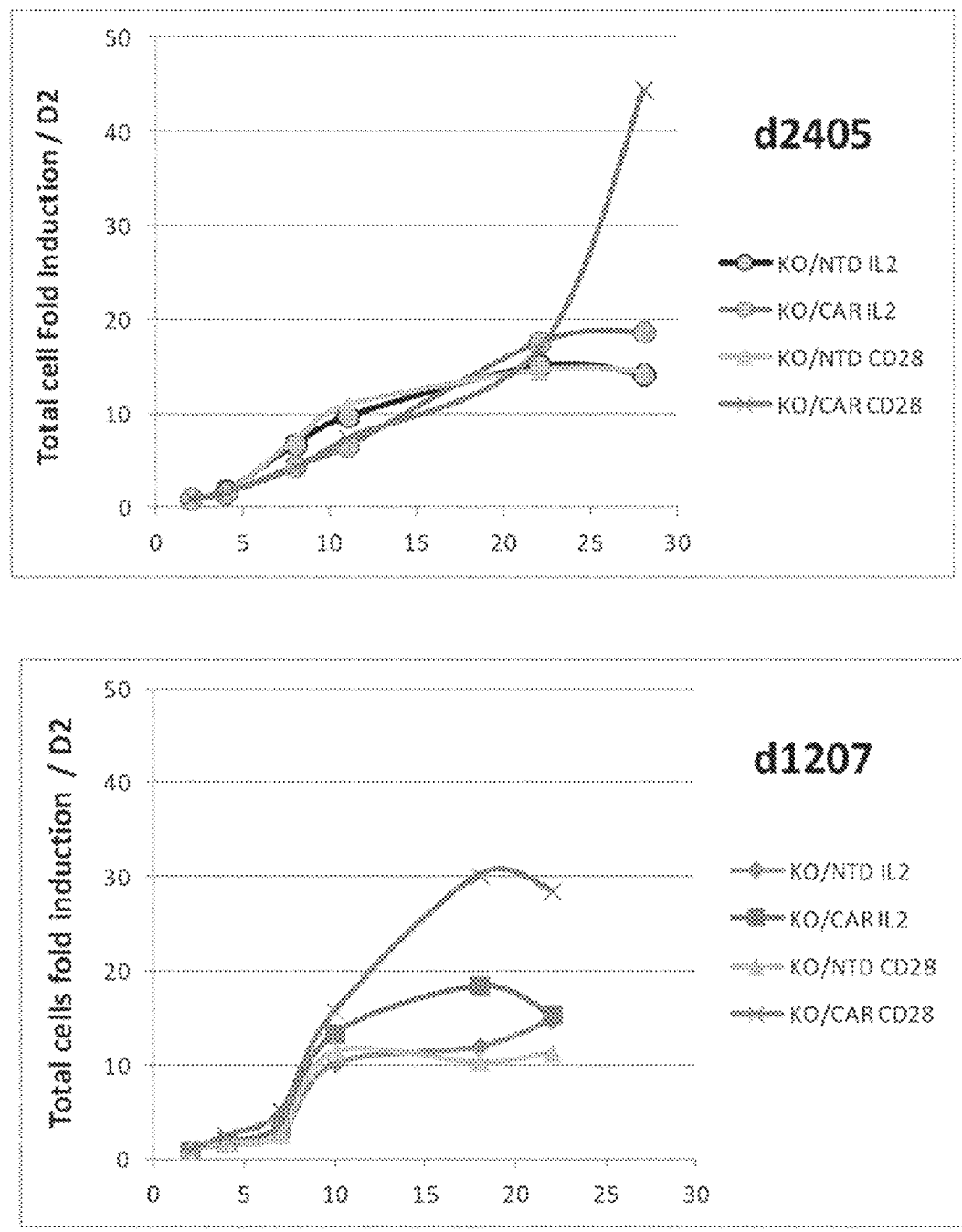
FIG. 1: Proliferation of TCR alpha inactivated T cells (KO) transduced with 4G7-CAR lentiviral vector compared to non transduced KO T cells (NTD). Proliferation was followed during 30 days after (IL2+CD28) or not (IL2) a step of reactivation with soluble anti-CD28.

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, New York: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

CD19 Specific Chimeric Antigen Receptor

The present invention relates to a chimeric antigen receptor (CAR) comprising an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

In a preferred embodiment, said extracellular ligand-binding domain comprises a single chain antibody fragment (scFv) comprising the light (VL) and the heavy (VH) variable fragment of a target antigen specific monoclonal antibody joined by a flexible linker. In a preferred embodiment, said scFV is derived from the CD19 monoclonal antibody 4G7 (Peipp, Saul et al. 2004), preferably said scFV of the present invention comprises a part of the CD19 monoclonal antibody 4G7 immunoglobulin gamma 1 heavy chain (GenBank®: CAD88275.1; SEQ ID NO: 1) and a part of the CD19 monoclonal antibody 4G7 immunoglobulin kappa light chain (GenBank®: CAD88204.1; SEQ ID NO: 2), preferably linked together by a flexible linker. In a preferred embodiment, said scFV of the present invention comprises the variable fragments of the CD19 monoclonal antibody 4G7 immunoglobulin gamma 1 heavy chain (SEQ ID NO: 3) and the variable fragments of the CD19 monoclonal antibody 4G7 immunoglobulin kappa light chain (SEQ ID NO: 4 or SEQ ID NO: 5) linked together by a flexible linker. In particular embodiment said flexible linker has the amino acid sequence (SEQ ID NO: 6).

In other words, said CAR comprises an extracellular ligand-biding domain which comprises a single chain FV fragment derived from a CD19 specific monoclonal antibody 4G7. In a particular embodiment, said scFV comprises a part of amino acid sequences selected from the group consisting of: SEQ ID NO: 1 to 5. In a preferred embodiment said scFV comprises at least 70%, preferably at least 80%, more preferably at least 90%, 95% 97% or 99% sequence identity with amino acid sequence selected from the group consisting of SEQ ID NO: 7 and SEQ ID NO: 8.

The signal transducing domain or intracellular signaling domain of the CAR according to the present invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function.

Preferred examples of signal transducing domain for use in a CAR can be the cytoplasmic sequences of the T cell receptor and co-receptors that act in concert to initiate signal transduction following antigen receptor engagement, as well as any derivate or variant of these sequences and any synthetic sequence that has the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the CAR can comprise the CD3zeta signaling domain which has amino acid sequence with at least 70%, preferably at least 80%, more preferably at least 90%, 95% 97% or 99% sequence identity with amino acid sequence selected from the group consisting of (SEQ ID NO: 10).

In particular embodiment the signal transduction domain of the CAR of the present invention comprises a co-stimulatory signal molecule. A co-stimulatory molecule is a cell surface molecule other than an antigen receptor or their ligands that is required for an efficient immune response. "Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MEW molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CO2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

In a preferred embodiment, the signal transduction domain of the CAR of the present invention comprises a part of co-stimulatory signal molecule selected from the group consisting of fragment of 4-1BB (GenBank®: AAA53133.) and CD28 (NP 006130.1). In particular the signal transduction domain of the CAR of the present invention comprises amino acid sequence which comprises at least 70%, preferably at least 80%, more preferably at least 90%, 95% 97% or 99% sequence identity with amino acid sequence selected from the group consisting of SEQ ID NO: 11 and SEQ ID NO: 12.

The CAR according to the present invention is expressed on the surface membrane of the cell. Thus, the CAR can comprise a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can be derived either from a natural or from a synthetic source. The transmembrane domain can be derived from any membrane-bound or transmembrane protein. As non limiting examples, the transmembrane polypeptide can be a subunit of the T cell receptor such as α, β, γ or δ, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine. In a preferred embodiment said transmembrane domain is derived from the human CD8 alpha chain (e.g. NP_001139345.1). The transmembrane domain can further comprise a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain (e.g. NP_001139345.1). In another particular embodiment, said transmembrane and hinge domains comprise a part of human CD8 alpha chain, preferably which comprises at least 70%, preferably at least SO %, more preferably at least 90%, 95% 97% or 99% sequence identity with amino acid sequence selected from the group consisting of SEQ ID NO: 13.

In a particular embodiment, said Chimeric Antigen Receptor of the present invention comprises a scFV derived from the CD19 monoclonal antibody 4G7, a CDS alpha human hinge and transmembrane domain, the CD3 zeta signaling domain and 4-1BB signaling domain. Preferably, the 4G7 CAR of the present invention comprises at least 70%, preferably at least 80%, more preferably at least 90%, 95% 97% or 99% sequence identity with amino acid sequence selected from the group consisting of SEQ ID NO: 14 and 15.

Downregulation or mutation of target antigens is commonly observed in cancer cells, creating antigen-loss escape variants. Thus, to offset tumor escape and render immune cell more specific to target, the CD19 specific CAR can comprise another extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

Polynucleotides, Vectors:

The present invention also relates to polynucleotides, vectors encoding the above described CAR according to the invention. In a preferred embodiment, the present invention relates to a polynucleotide comprising the nucleic acid sequence SEQ ID NO: 17. In a preferred embodiment, the polynucleotide has at least 70%, preferably at least 80%, more preferably at least 90%, 95% 97% or 99% sequence identity with nucleic acid sequence selected from the group consisting of SEQ ID NO: 17.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

In a particular embodiment, the different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct, transmembrane polypeptide into the secretory pathway of a host cell, a secretory signal sequence (also known as a leader sequence, prepro sequence or pre sequence) is provided in polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the amino acid sequence SEQ ID NO: 18 and 19.

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

In a preferred embodiment, the polynucleotide according to the present invention comprises the nucleic acid sequence selected from the group consisting of: SEQ ID NO: 17. The present invention relates to polynucleotides comprising a nucleic acid sequence that has at least 70%, preferably at least 80%, more preferably at least 90%, 95% 97% or 99% sequence identity with nucleic acid sequence selected from the group consisting of SEQ ID NO: 17.

Methods of Engineering an Immune Cell:

In encompassed particular embodiment, the invention relates to a method of preparing immune cells for immunotherapy comprising introducing into said immune cells the CAR according to the present invention and expanding said cells. In particular embodiment, the invention relates to a method of engineering an immune cell comprising providing a cell and expressing at the surface of said cell at least one CAR as described above. In particular embodiment, the method comprises transforming the cell with at least one polynucleotide encoding CAR as described above, and expressing said polynucleotides into said cell.

In a preferred embodiment, said polynucleotides are included in lentiviral vectors in view of being stably expressed in the cells.

In another embodiment, said method further comprises a step of genetically modifying said cell by inactivating at least one gene expressing one component of the TCR, a target for an immunosuppressive agent, HLA gene and/or an immune checkpoint gene such as PDCD1 or CTLA-4. In a preferred embodiment, said gene is selected from the group consisting of TCRalpha, TCRbeta, CD52, GR, PD1 and CTLA-4. In a preferred embodiment said method further comprises introducing into said T cells a rare-cutting endonuclease able to selectively inactivate by DNA cleavage said genes. In a more preferred embodiment said rare-cutting endonuclease is TALE-nuclease or Cas9 endonuclease.

Delivery Methods

The different methods described above involve introducing CAR into a cell. As non-limiting example, said CAR can be introduced as transgenes encoded by one plasmidic vector. Said plasmid vector can also contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Engineered Immune Cells

The present invention also relates to isolated cells or cell lines susceptible to be obtained by said method to engineer cells. In particular said isolated cell comprises at least one CAR as described above. In another embodiment, said isolated cell comprises a population of CARs each one comprising different extracellular ligand binding domains. In particular, said isolated cell comprises exogenous polynucleotide sequence encoding CAR. Genetically modified immune cells of the present invention are activated and proliferate independently of antigen binding mechanisms.

In the scope of the present invention is also encompassed an isolated immune cell, preferably a T-cell obtained according to any one of the methods previously described. Said immune cell refers to a cell of hematopoietic origin functionally involved in the initiation and/or execution of innate and/or adaptative immune response. Said immune cell according to the present invention can be derived from a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

In another embodiment, said isolated cell according to the present invention comprises a polynucleotide encoding CAR.

Activation and Expansion of T Cells

Whether prior to or after genetic modification of the T cells, even if the genetically modified immune cells of the present invention are activated and proliferate independently of antigen binding mechanisms, the immune cells, particularly T-cells of the present invention can be further activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with an agent that stimulates a CD3 TCR complex and a co-stimulatory molecule on the surface of the T cells to create an activation signal for the T-cell.

For example, chemicals such as calcium ionophore A23187, phorbol 12-myristate 13-acetate (PMA), or mitogenic lectins like phytohemagglutinin (PHA) can be used to create an activation signal for the T-cell.

As non limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, -10, -2, IL-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Applications

In another embodiment, isolated cell obtained by the different methods or cell line derived from said isolated cell as previously described can be used as a medicament. In another embodiment, said medicament can be used for treating cancer, particularly for the treatment of B-cell lymphomas and leukemia in a patient in need thereof. In another embodiment, said isolated cell according to the invention or cell line derived from said isolated cell can be used in the manufacture of a medicament for treatment of a cancer in a patient in need thereof.

In another aspect, the present invention relies on methods for treating patients in need thereof, said method comprising at least one of the following steps:

(a) providing an immune-cell obtainable by any one of the methods previously described;

(b) Administrating said transformed immune cells to said patient,

On one embodiment, said T cells of the invention can undergo robust in vivo T cell expansion and can persist for an extended amount of time.

Said treatment can be ameliorating, curative or prophylactic. It may be either part of an autologous immunotherapy or part of an allogeneic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

Cells that can be used with the disclosed methods are described in the previous section. Said treatment can be used to treat patients diagnosed with cancer. Cancers that may be treated may comprise nonsolid tumors (such as hematological tumors, including but not limited to pre-B ALL (pediatric indication), adult ALL, mantle cell lymphoma, diffuse large B-cell lymphoma and the like. Types of cancers to be treated with the CARs of the invention include, but are not limited to certain leukemia or lymphoid malignancies. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH (alemtuzumab), anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH (alemtuzumab), In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Other Definitions

Unless otherwise specified, "a," "an," "the," and "at least one" are used interchangeably and mean one or more than one.—Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

By chimeric antigen receptor (CAR) is intended molecules that combine a binding domain against a component present on the target cell, for example an anti body-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFcζ) and have the ability, when expressed in T cells, to redirect antigen recognition based on the monoclonal antibody's specificity. One example of CAR used in the present invention is a CAR directing against CD19 antigen and can comprise as non limiting example the amino acid sequence: SEQ ID NO: 14.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Perrin, Buckle et al. 1993; Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005), a Cas9 endonuclease from CRISPR system (Gasiunas, Barrangou et al. 2012; Jinek, Chylinski et al. 2012; Cong, Ran et al. 2013; Mali, Yang et al. 2013) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al. 2011). Engineered TAL-nucleases are commercially available under the trade name TALEN™ (Cellectis, 8 rue de la Croix Jarry, 75013 Paris, France).

The rare-cutting endonuclease according to the present invention can also be a Cas9 endonuclease. Recently, a new genome engineering tool has been developed based on the RNA-guided Cas9 nuclease (Gasiunas, Barrangou et al. 2012; Jinek, Chylinski et al. 2012; Cong, Ran et al. 2013; Mali, Yang et al. 2013) from the type II prokaryotic CRISPR (Clustered Regularly Interspaced Short palindromic Repeats) adaptive immune system (see for review (Sorek, Lawrence et al. 2013)). The CRISPR Associated (Cas) system was first discovered in bacteria and functions as a defense against foreign DNA, either viral or plasmid. CRISPR-mediated genome engineering first proceeds by the selection of target sequence often flanked by a short sequence motif, referred as the protospacer adjacent motif (PAM). Following target sequence selection, a specific crRNA, complementary to this target sequence is engineered. Trans-activating crRNA (tracrRNA) required in the CRISPR type II systems paired to the crRNA and bound to the provided Cas9 protein. Cas9 acts as a molecular anchor facilitating the base pairing of tracRNA with cRNA (Deltcheva, Chylinski et al. 2011). In this ternary complex, the dual tracrRNA: crRNA structure acts as guide RNA that directs the endonuclease Cas9 to the cognate target sequence. Target recognition by the Cas9-tracrRNA:crRNA complex is initiated by scanning the target sequence for homology between the target sequence and the crRNA. In addition to the target sequence-crRNA complementarity, DNA targeting requires the presence of a short motif adjacent to the protospacer (protospacer adjacent motif—PAM). Following pairing between the dual-RNA and the target sequence, Cas9 subsequently introduces a blunt double strand break 3 bases upstream of the PAM motif (Garneau, Dupuis et al. 2010).

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-Crel variant.

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e.g. adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as nonlimiting example, that are able to integrate the genome of a target cell. At the opposite by "non-integrative lentiviral vectors (or NILV)" is meant efficient gene delivery vectors that do not integrate the genome of a target cell through the action of the virus integrase.

Delivery vectors and vectors can be associated or combined with any cellular permeabilization techniques such as sonoporation or electroporation or derivatives of these techniques.

By cell or cells is int ended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRCS cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, or higher or lower activity.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"similarity" describes the relationship between the amino acid sequences of two or more polypeptides. BLASTP may also be used to identify an amino acid sequence having at least 70%, 75%, 80%, 85%, 87.5%, 90%, 92.5%, 95%, 97.5%, 98%, 99% sequence similarity to a reference amino acid sequence using a similarity matrix such as BLOSUM45, BLOSUM62 or BLOSUM80. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means. A polynucleotide encoding such a functional variant would be produced by reverse translating its amino acid sequence using the genetic code.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory igand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/

CD3 ligation, leads to T cell proliferation and/or upregulation or downregulation of key molecules.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1: Proliferation of TCRalpha Inactivated Cells Expressing a 4G7-CAR

Heterodimeric TALE-nuclease targeting two 17-bp long sequences (called half targets) separated by an 15-bp spacer within T-cell receptor alpha constant chain region (TRAC) gene were designed and produced. Each half target is recognized by repeats of the half TALE-nucleases listed in Table 1.

| Target | Target sequence | Repeat sequence | Half TALE-nuclease |
|---|---|---|---|
| TRAC_T01 | TTGTCCCAC AGATATCC Agaaccctg accctg CCGTGTACC AGCTGAGA (SEQ ID NO: 20) | Repeat TRAC_T01-L (SEQ ID NO: 21) Repeat TRAC_T01-R (SEQ ID NO: 22) | TRAC_T01-L TALEN (SEQ ID NO: 23) TRAC_T01-R TALEN (SEQ ID NO: 24) |

Each TALE-nuclease construct was subcloned using restriction enzyme digestion in a mammalian expression vector under the control of the T7 promoter. mRNA encoding TALE-nuclease cleaving TRAC genomic sequence were synthesized from plasmid carrying the coding sequence downstream from the T7 promoter.

Purified T cells preactivated during 72 hours with antiCD3/CD28 coated beads were transfected with each of the 2 mRNAs encoding both half TRAC_T01 TALE-nucleases. 48 hours post-transfection, T cells were transduced with a lentiviral vector encoding 4G7-CAR (SEQ ID NO: 14). 2 days post-transduction, CD3NEG cells were purified using anti-CD3 magnetic beads and 5 days post-transduction cells were reactivated with soluble anti-CD28 (5 µg/ml).

Cell proliferation was followed for up to 30 days after reactivation by counting cell 2 times per week. The FIG. 1 shows the fold induction in cell number respect to the amount of cells present at day 2 post reactivation for two different donors. Increased proliferation in TCR alpha inactivated cells expressing the 4G7-CAR, especially when reactivated with anti-CD28, was observed compared to non transduced cells.

Figure 2:
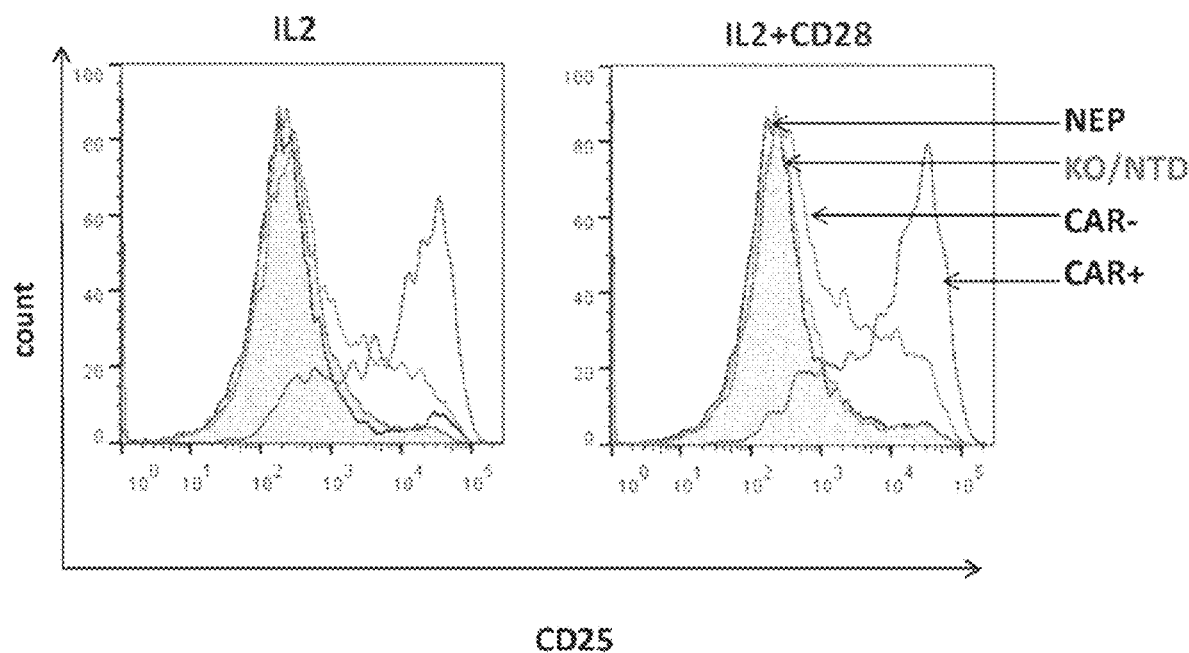
FIG. 2: CD25 activation marker expression analysis at the surface of inactivated TCR alpha T cells transduced with 4G7-CAR lentiviral vector, gated on the basis of 4G7-CAR expression (CAR+, CAR−) and compared to CD25 expression on TCR alpha positive non electroporated (NEP) or TCR alpha disrupted but non tranduced (NTD) cells. CD25 expression was analyzed after (IL2+CD28) or not (IL2) a step of reactivation with soluble anti-CD28.

To investigate whether the human T cells expressing the 4G7-CAR display activated state, the expression of the activation marker CD25 was analyzed by FACS 7 days post transduction. As indicated in FIG. 2, purified cells transduced with the lentiviral vector encoding 4G7-CAR expressed considerably more CD25 at their surface than the non transduced cells. Increased CD25 expression is observed both in CD28 reactivation or no reactivation conditions.

Example 2: Comparison of Basal Activation of Primary Human T Cells Expressing the 4G7-CAR and the Classical FMC63-CAR To determine whether 4G7 scFV confers a prolonged "activated" state on the transduced cell, basal activation of T cell transduced with CAR harboring a 4G7 scFV (SEQ ID NO: 17 encoded SEQ ID NO: 15) or a classical FMC63 scFV (SEQ ID NO: 16) was compared.

Purified human T cells were transduced according to the following protocol: briefly, $1 \times 10^6$ CD3+ cells preactivated during 3 days with anti CD3/CD28 coated beads and recombinant IL2 were transduced with lentiviral vectors encoding the 4G7-CAR (SEQ ID NO: 15) and the FMC63-CAR (SEQ ID NO: 16) at an MOI of 5 in 12-well non tissue culture plates coated with 30 µg/ml retronectin. 24 hours post transduction the medium was removed and replaced by fresh medium. The cells were then maintained at a concentration of $1 \times 10^6$ cells/ml throughout the culture period by cell enumeration every 2-3 days.

Figure 3:
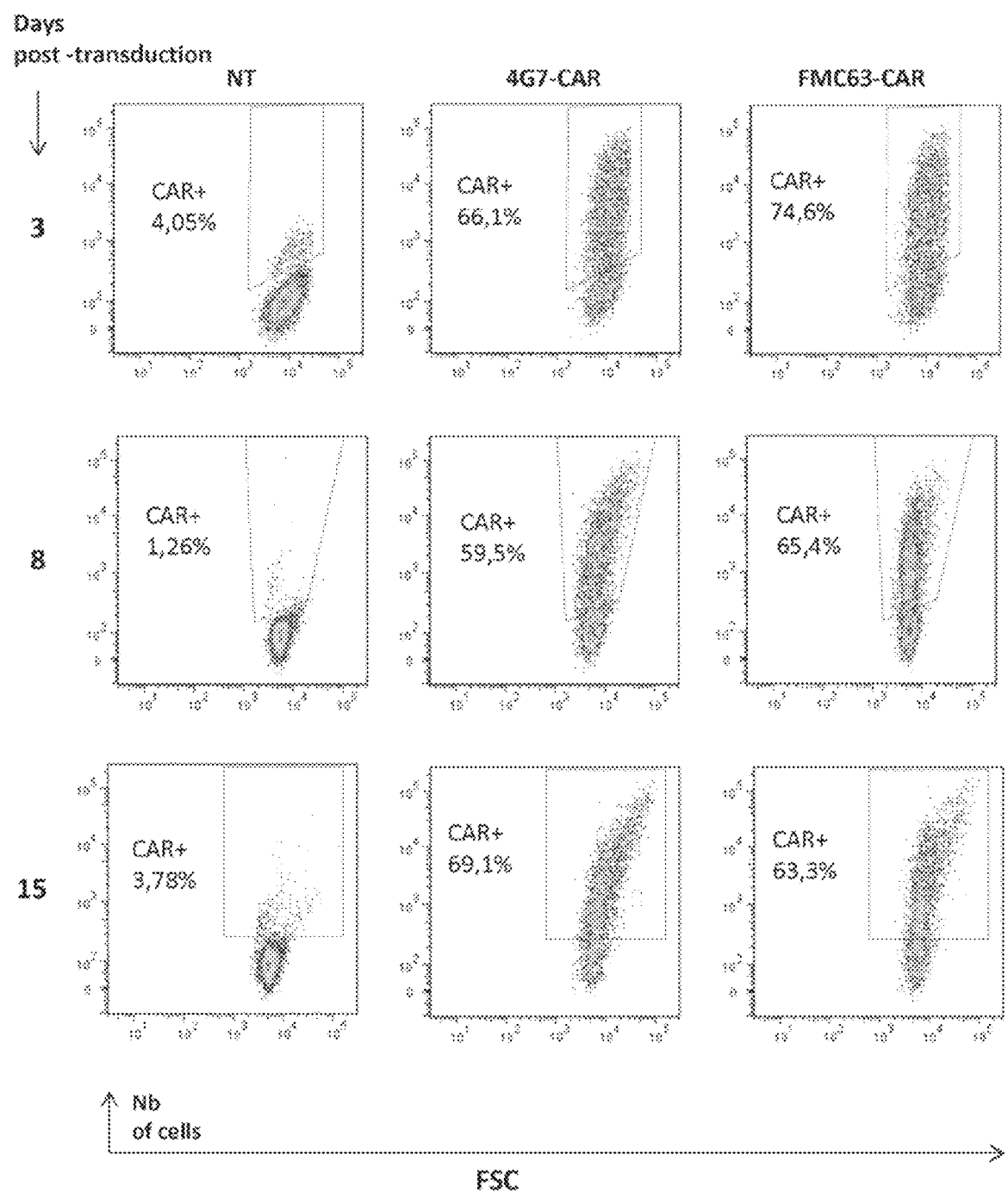
FIG. 3: CAR expression analysis at the surface of T cells transduced with a lentiviral vector encoding either the 4G7-CAR or the FMC63-CAR. The analysis was done 3, 8 and 15 days post transduction by flow cytometry. NT refers to no transduced T cells.

3, 8 and 15 days post transduction with the lentiviral vector encoding either the 4G7-CAR or the FMC63-CAR, the percentage of CAR expressing cells was assessed by flow cytometry. It was observed that the efficiency of transduction was relatively equivalent with the two lentiviral vectors FIG. 3.

Figure 4:
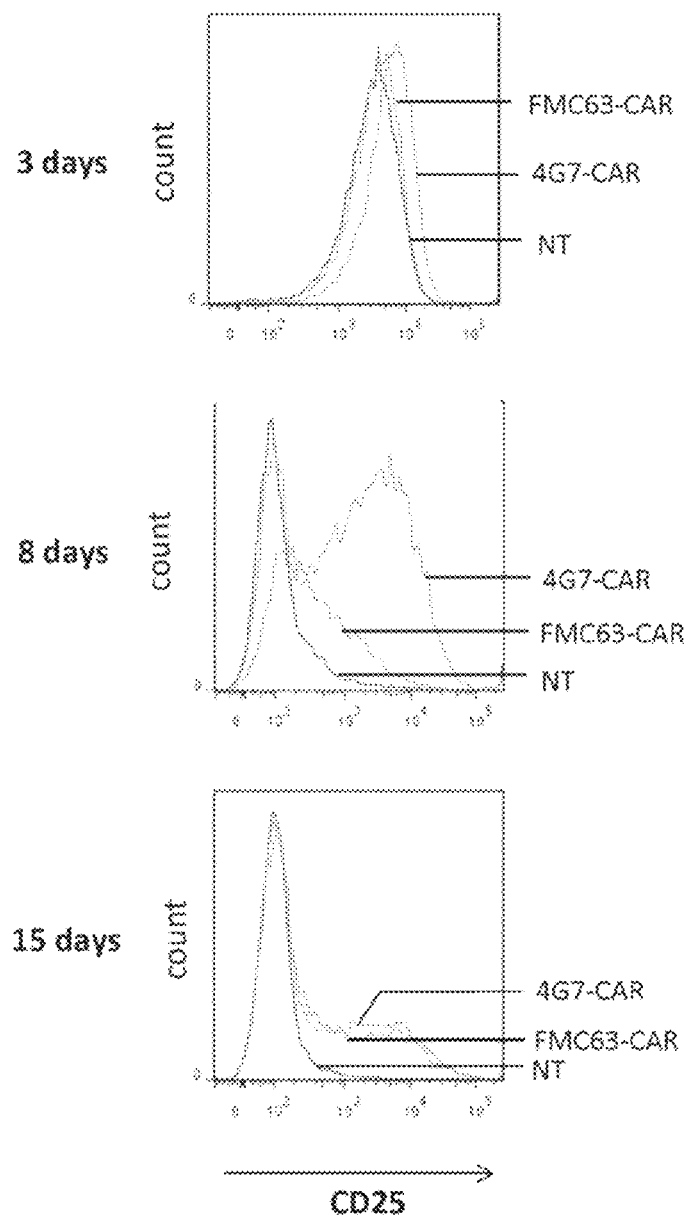
FIG. 4: CD25 expression analysis at the surface of T cells transduced with a lentiviral vector encoding either the 4G7-CAR or the FMC63-CAR. The analysis was done 3, 8 and 15 days post transduction by flow cytometry. NT refers to no transduced T cells.

It was then investigated whether the human T cells expressing the 4G7-CAR exhibited a more activated state than the human T cells expressing the FMC63-CAR. For that purpose the expression of the activation marker CD25 was compared at the surface of T cells transduced with the 2 lentiviral vectors at different time points. As indicated in the FIG. 4, 3 and 8 days post transduction, the cells transduced with the lentiviral vector encoding the 4G7-CAR expressed considerably more CD25 at their surface than the cells transduced with the lentiviral vector encoding the FMC63-CAR.

Figure 5:
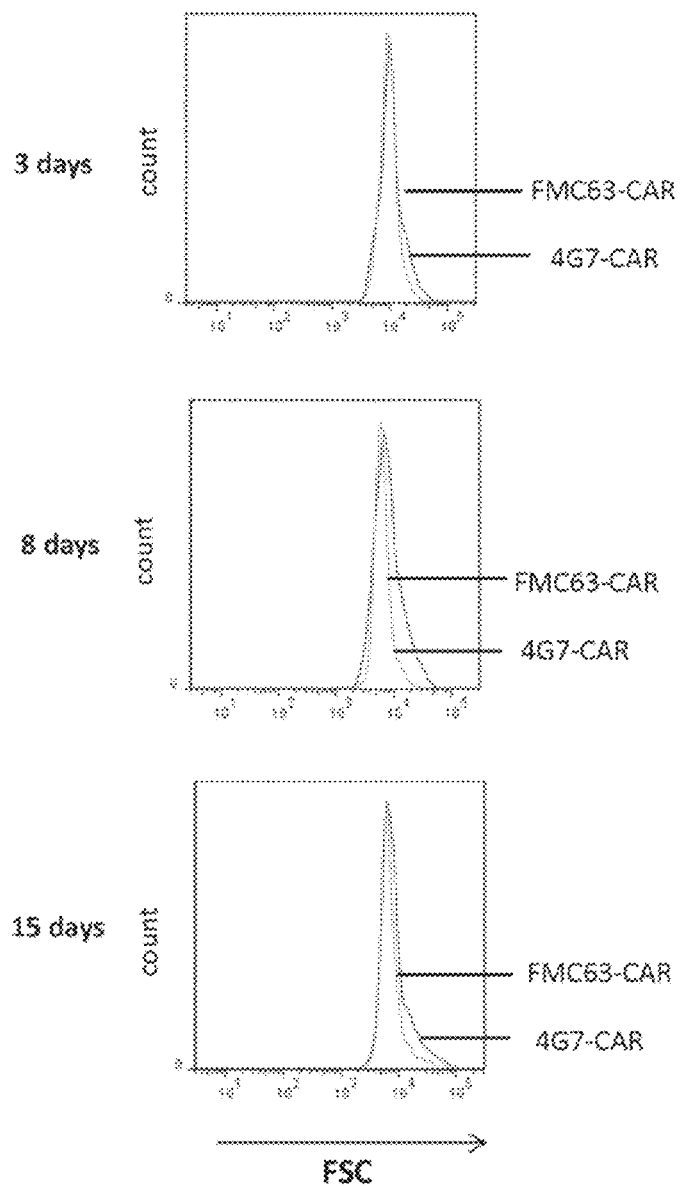
FIG. 5: Size analysis of T cells transduced with a lentiviral vector encoding either the 4G7-CAR or the FMC63-CAR. The analysis was done 3, 8 and 15 days post transduction by flow cytometry. NT refers to no transduced T cells.

The size of the 4G7-CAR or FMC63-CAR transduced cells was also assessed by flow cytometry at different time points. It was observed that the cells expressing the 4G7-CAR were bigger than the cells expressing the FMC63-CAR 3, 8 and 15 days post transduction FIG. 5.

Following non-specific activation in vitro, 4G7-CAR transduced cells display an increased cell size (blast formation) as well as the expression of activation markers (CD25) over an extended time period. This long-term activation permits extended proliferation compared to cells transduced with a similar CAR containing the FMC63 ScFv.

Figure 6:
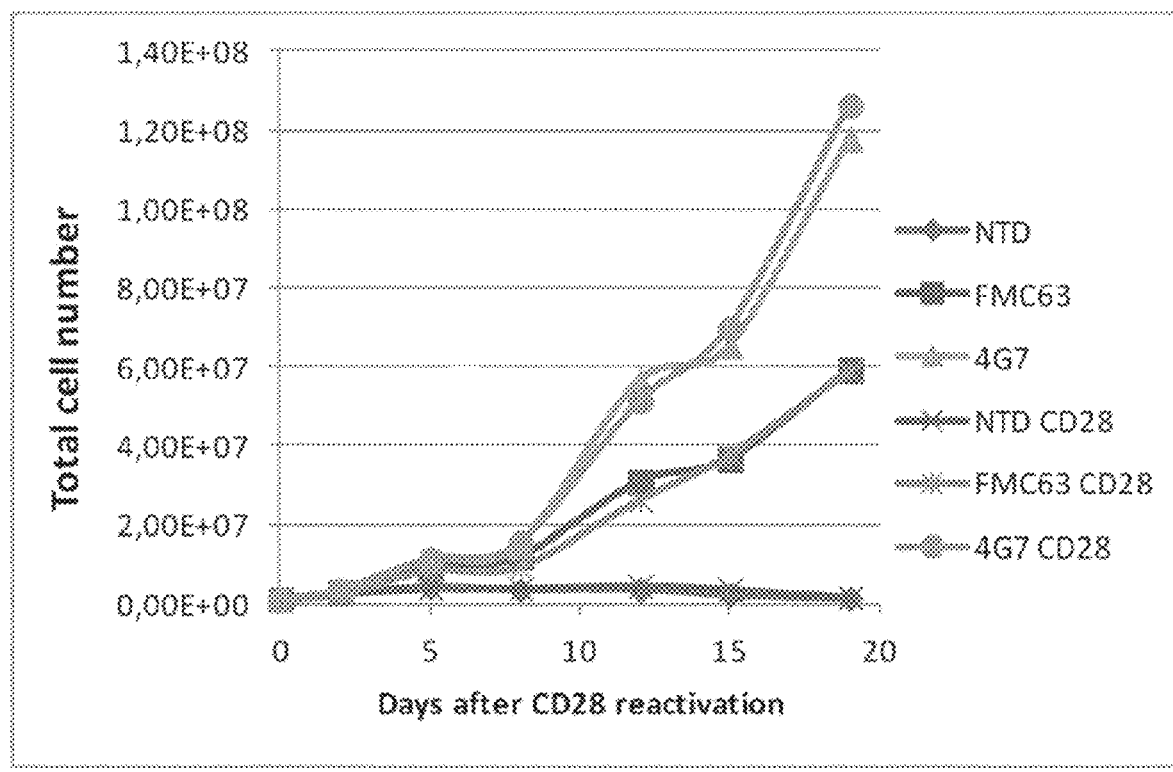
FIG. 6: Proliferation of T cells transduced with 4G7-CAR compared to FMC63 lentiviral vector. Proliferation was followed during 20 days after (CD28) or not (−) a step of reactivation with soluble anti-CD28. NTD refers to no transduced T cells.

Example 3: Comparison of Proliferation of Primary Human T Cells Expressing the 4G7-CAR and the Classical FMC63-CAR To determine whether 4G7 scFV confers a higher proliferation activity, proliferation of T cell transduced with CAR harboring a 4G7 scFV (SEQ ID NO: 17 encoded SEQ ID NO: 15) or a classical FMC63 scFV (SEQ ID NO: 16) was followed up to 20 days by counting cell two times per week. Purified human T cells were transduced according to the following protocol: briefly, $1 \times 10^6$ CD3+ cells preactivated during 3 days with anti CD3/CD28 coated beads and recombinant IL2 were transduced with lentiviral vectors encoding the 4G7-CAR (SEQ ID NO: 15) and the FMC63-CAR (SEQ ID NO: 16). The cells were then maintained under classical conditions and were reactivated at Day 12. Cells were seeded at the same density and were counted two times per week during 20 days. As represented in FIG. 6, proliferation activity of T-cells expressing the 4G7-CAR is twofold higher compared to those of cells expressing the classical FMC63-CAR.

REFERENCES

Arimondo, P. B., C. J. Thomas, et al. (2006). "Exploring the cellular activity of camptothecin-triple-helix-forming oligonucleotide conjugates." Mol Cell Biol 26(1): 324-33.

Atkins, J. F., N. M. Wills, et al. (2007). "A case for "StopGo": reprogramming translation to augment codon meaning of GGN by promoting unconventional termination (Stop) after addition of glycine and then allowing continued translation (Go)." Rna 13(6): 803-10.

Bierer, B. E., G. Hollander, et al. (1993). "Cyclosporin A and FK506: molecular mechanisms of immunosuppression and probes for transplantation biology." Curr Opin Immunol 5(5): 763-73.

Boch, J., H. Scholze, et al. (2009). "Breaking the code of DNA binding specificity of TAL-type Ill effectors." Science 326(5959): 1509-12.

Choulika, A., A. Perrin, et al. (1995). "Induction of homologous recombination in mammalian chromosomes by using the I-Scel system of Saccharomyces cerevisiae." Mol Cell Biol 15(4): 1968-73.

Christian, M., T. Cermak, et al. (2010). "Targeting DNA double-strand breaks with TAL effector nucleases." Genetics 186(2): 757-61.

Cong, L., F. A. Ran, et al. (2013). "Multiplex genome engineering using CRISPR/Cas systems." Science 339 (6121): 819-23.

Deltcheva, E., K. Chylinski, et al. (2011). "CRISPR RNA maturation by trans-encoded small RNA and host factor RNase III." Nature 471(7340): 602-7.

Donnelly, M. and G. Elliott (2001). "Nuclear localization and shuttling of herpes simplex virus tegument protein VP13/14." J Virol 75(6): 2566-74.

Doronina, V. A., C. Wu, et al. (2008). "Site-specific release of nascent chains from ribosomes at a sense codon." Mol Cell Biol 28(13): 4227-39.

Eisenschmidt, K., T. Lanio, et al. (2005). "Developing a programmed restriction endonuclease for highly specific DNA cleavage." Nucleic Acids Res 33(22): 7039-47.

Garneau, J. E., M. E. Dupuis, et al. (2010). "The CRISPR/Cas bacterial immune system cleaves bacteriophage and plasmid DNA." Nature 468(7320): 67-71.

Gasiunas, G., R. Barrangou, et al. (2012). "Cas9-crRNA ribonucleoprotein complex mediates specific DNA cleavage for adaptive immunity in bacteria." Proc Natl Acad Sci USA 109(39): E2579-86.

Henderson, D. J., I. Naya, et al. (1991). "Comparison of the effects of FK-506, cyclosporin A and rapamycin on IL-2 production." Immunology 73(3): 316-21.

Jena, B., G. Dotti, et al. (2010). "Redirecting T-cell specificity by introducing a tumor-specific chimeric antigen receptor." Blood 116(7): 1035-44.

Jinek, M., K. Chylinski, et al. (2012). "A programmable dual-RNA-guided DNA endonuclease in adaptive bacterial immunity." Science 337(6096): 816-21.

Kalish, J. M. and P. M. Glazer (2005). "Targeted genome modification via triple helix formation." Ann NY Acad Sci 1058: 151-61.

Li, T., S. Huang, et al. (2011). "TAL nucleases (TALNs): hybrid proteins composed of TAL effectors and Fokl DNA-cleavage domain." Nucleic Acids Res 39(1): 359-72.

Liu, J., M. W. Albers, et al. (1992). "Inhibition of T cell signaling by immunophilin-ligand complexes correlates with loss of calcineurin phosphatase activity." Biochemistry 31(16): 3896-901.

Mali, P., L. Yang, et al. (2013). "RNA-guided human genome engineering via Cas9." Science 339(6121): 823-6.

Moscou, M. J. and A. J. Bogdanove (2009). "A simple cipher governs DNA recognition by TAL effectors." Science 326(5959): 1501.

Paques, F. and P. Duchateau (2007). "Meganucleases and DNA double-strand break-induced recombination: perspectives for gene therapy." Curr Gene Ther 7(1): 49-66.

Park, T. S., S. A. Rosenberg, et al. (2011). "Treating cancer with genetically engineered T cells." Trends Biotechnol 29(11): 550-7.

Peipp, M., D. Saul, et al. (2004). "Efficient eukaryotic expression of fluorescent scFv fusion proteins directed against CD antigens for FACS applications." J Immunol Methods 285(2): 265-80.

Perrin, A., M. Buckle, et al. (1993). "Asymmetrical recognition and activity of the I-Scel endonuclease on its site and on intron-exon junctions." Embo J 12(7): 2939-47.

Pingoud, A. and G. H. Silva (2007). "Precision genome surgery." Nat Biotechnol 25(7): 743-4.

Porteus, M. H. and D. Carroll (2005). "Gene targeting using zinc finger nucleases." Nat Biotechnol 23(8): 967-73.

Rouet, P., F. Smih, et al. (1994). "Introduction of double-strand breaks into the genome of mouse cells by expression of a rare-cutting endonuclease." Mol Cell Biol 14(12): 8096-106.

Sorek, R., C. M. Lawrence, et al. (2013). "CRISPR-mediated Adaptive Immune Systems in Bacteria and Archaea." Annu Rev Biochem.

Stoddard, B. L. (2005). "Homing endonuclease structure and function." Q Rev Biophys 38(1):49-95.

What is claimed is:

1. A method of treating cancer, the method comprising administering to a subject having a cancer expressing CD19 a genetically modified T cell with at least one effector function, wherein the genetically modified T-cell expresses a CD19-specific chimeric antigen receptor (CAR) comprising, in order from N-terminus to C-terminus:
   i) the amino acid sequence of SEQ ID NO: 7;
   ii) the amino acid sequence of SEQ ID NO: 13;
   iii) the amino acid sequence of SEQ ID NO: 11; and
   iv) the amino acid sequence of SEQ ID NO: 10.

2. The method of claim 1, wherein the cancer is a non-solid tumor.

3. The method of claim 1, wherein the cancer is a B-cell lymphoma or leukemia.

4. The method of claim 1, wherein the genetically modified T cell administered to the subject is an allogeneic T cell.

5. The method of claim 1, wherein the genetically modified T cell administered to the subject is engineered from a cell of a healthy donor.

6. The method of claim 1, wherein the genetically modified T cell administered to the subject is a cytotoxic T lymphocyte (CTL).

7. The method of claim 1, wherein $10^4$-$10^9$ of the genetically modified T cells per kg body weight are administered to the subject.

8. The method of claim 1, wherein the genetically modified T cell is administered intravenously to the subject.

9. The method of claim 1, comprising administering alemtuzumab to the subject before, during, and/or after administration of the genetically modified T cell.

10. The method of claim 1, wherein the CAR further comprises the amino acid sequence of SEQ ID NO: 18 at the N-terminus.

* * * * *